United States Patent
Fernandes et al.

(10) Patent No.: US 12,349,910 B2
(45) Date of Patent: Jul. 8, 2025

(54) SURGICAL STAPLE CARTRIDGE FOR SUPPORTING SURGICAL BUTTRESS MATERIAL

(71) Applicant: Covidien LP, Mansfield, MA (US)

(72) Inventors: Roanit Fernandes, Hamden, CT (US); Suresh Kumar Prema Mohanasundaram, Cheshire, CT (US); Jitendra Bhargava Srinivas, Hyderabad (IN); Matthew J. Chowaniec, Madison, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/589,980

(22) Filed: Feb. 28, 2024

(65) Prior Publication Data
US 2024/0197319 A1   Jun. 20, 2024

Related U.S. Application Data

(60) Continuation of application No. 17/679,162, filed on Feb. 24, 2022, now Pat. No. 11,918,218, which is a
(Continued)

(51) Int. Cl.
*A61B 17/072*   (2006.01)
*A61B 17/04*   (2006.01)
(Continued)

(52) U.S. Cl.
CPC .... *A61B 17/07292* (2013.01); *A61B 17/0467* (2013.01); *A61B 2017/00004* (2013.01);
(Continued)

(58) Field of Classification Search
CPC ................................................ A61B 17/07292
See application file for complete search history.

(56) References Cited

U.S. PATENT DOCUMENTS 5,915,616 A   6/1999   Viola et al.
5,964,394 A   10/1999   Robertson
(Continued)

FOREIGN PATENT DOCUMENTS

EP   2236099 A1   10/2010
EP   2630922 A1   8/2013
(Continued)

OTHER PUBLICATIONS

Extended European Search Report issued in corresponding European Application No. 21151625.7 dated Sep. 1, 2021, 10 pages.
(Continued)

*Primary Examiner* — Nathaniel C Chukwurah

(57) ABSTRACT

An end effector for use with a surgical stapler includes a staple cartridge assembly movable relative to an anvil assembly. The staple cartridge assembly defines a plurality of retention slots and a cavity. The staple cartridge assembly includes a plurality of staples, a plurality of pushers, an actuation sled, a surgical buttress material, a suture, and an anchoring button. The actuation sled is configured for movement along a length of the staple cartridge assembly to sequentially engage the plurality of pushers to eject the plurality of staples through the respective plurality of retention slots. The anchoring button is configured to be received in the cavity of the staple cartridge assembly such that a portion of the suture is supported in the cavity to be severed by a knife blade of the actuation sled when the actuation sled is advanced distally.

20 Claims, 16 Drawing Sheets

Related U.S. Application Data division of application No. 16/748,899, filed on Jan. 22, 2020, now Pat. No. 11,272,937.

(51) Int. Cl.
    *A61B 17/00*    (2006.01)
    *A61B 17/06*    (2006.01)

(52) U.S. Cl.
    CPC ............... *A61B 2017/0409* (2013.01); *A61B 2017/0618* (2013.01); *A61B 2017/07257* (2013.01); *A61B 2017/07271* (2013.01); *A61B 2017/07278* (2013.01)

(56) References Cited

U.S. PATENT DOCUMENTS

| | | |
|---|---|---|
| 7,128,253 B2 | 10/2006 | Mastri et al. |
| 7,334,717 B2 | 2/2008 | Rethy et al. |
| 7,819,896 B2 | 10/2010 | Racenet |
| 8,256,656 B2 | 9/2012 | Milliman et al. |
| 9,016,539 B2 | 4/2015 | Kostrzewski et al. |
| 9,345,479 B2 | 5/2016 | (Tarinelli) Racenet et al. |
| 9,486,215 B2 | 11/2016 | Olson et al. |
| 11,272,937 B2 | 3/2022 | Fernandes et al. |
| 11,918,218 B2 | 3/2024 | Fernandes et al. |
| 2009/0134200 A1* | 5/2009 | Tarinelli ........... A61B 17/07207 227/176.1 |
| 2010/0012704 A1* | 1/2010 | Tarinelli Racenet .................. A61B 17/068 227/180.1 |
| 2010/0243707 A1* | 9/2010 | Olson ............... A61B 17/07292 227/176.1 |
| 2010/0243708 A1 | 9/2010 | Aranyi et al. |
| 2011/0215132 A1* | 9/2011 | Aranyi ............. A61B 17/07207 227/176.1 |
| 2013/0022106 A1 | 1/2013 | Pao |
| 2013/0274722 A1 | 10/2013 | Kostrzewski et al. |
| 2015/0122872 A1 | 5/2015 | Olson et al. |

FOREIGN PATENT DOCUMENTS

| | | |
|---|---|---|
| EP | 2005894 B1 | 8/2014 |
| EP | 2772197 A1 | 9/2014 |
| JP | 2013-215578 A | 10/2013 |

OTHER PUBLICATIONS

Partial European Search Report issued in European Patent Application No. 21151625.7, dated Jun. 1, 2021.
Japanese Office Action for JP Application No. 2021-00730 mailed Aug. 13, 2024 (6 pages), Translation included.
Notice of Allowance for Japanese Patent Application No. 2021-000730 mailed Nov. 22, 2024, 6 pages.
Extended European Search Report for European Patent Application No. 24216697.3 mailed Mar. 20, 2025, 8 pages.

* cited by examiner

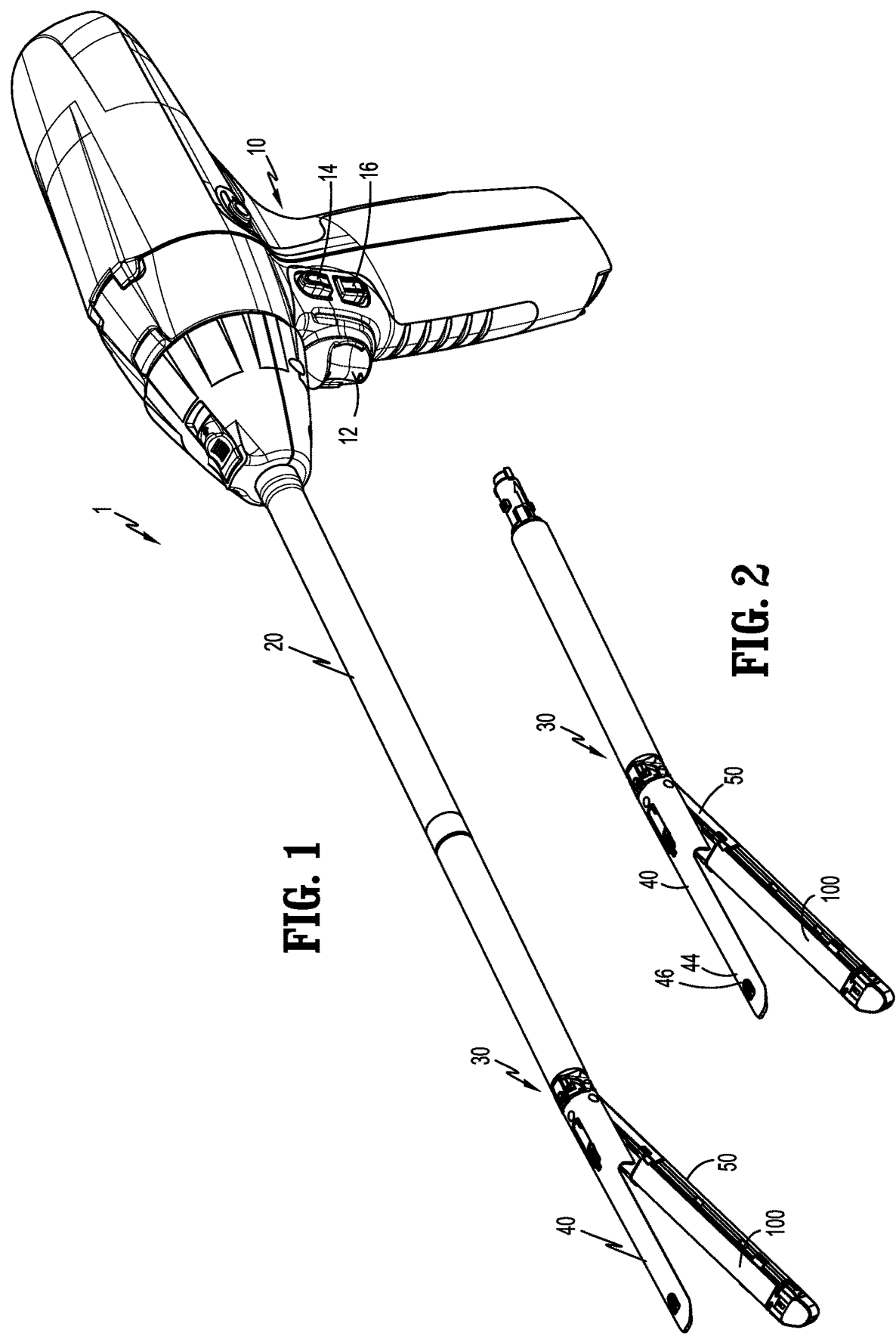

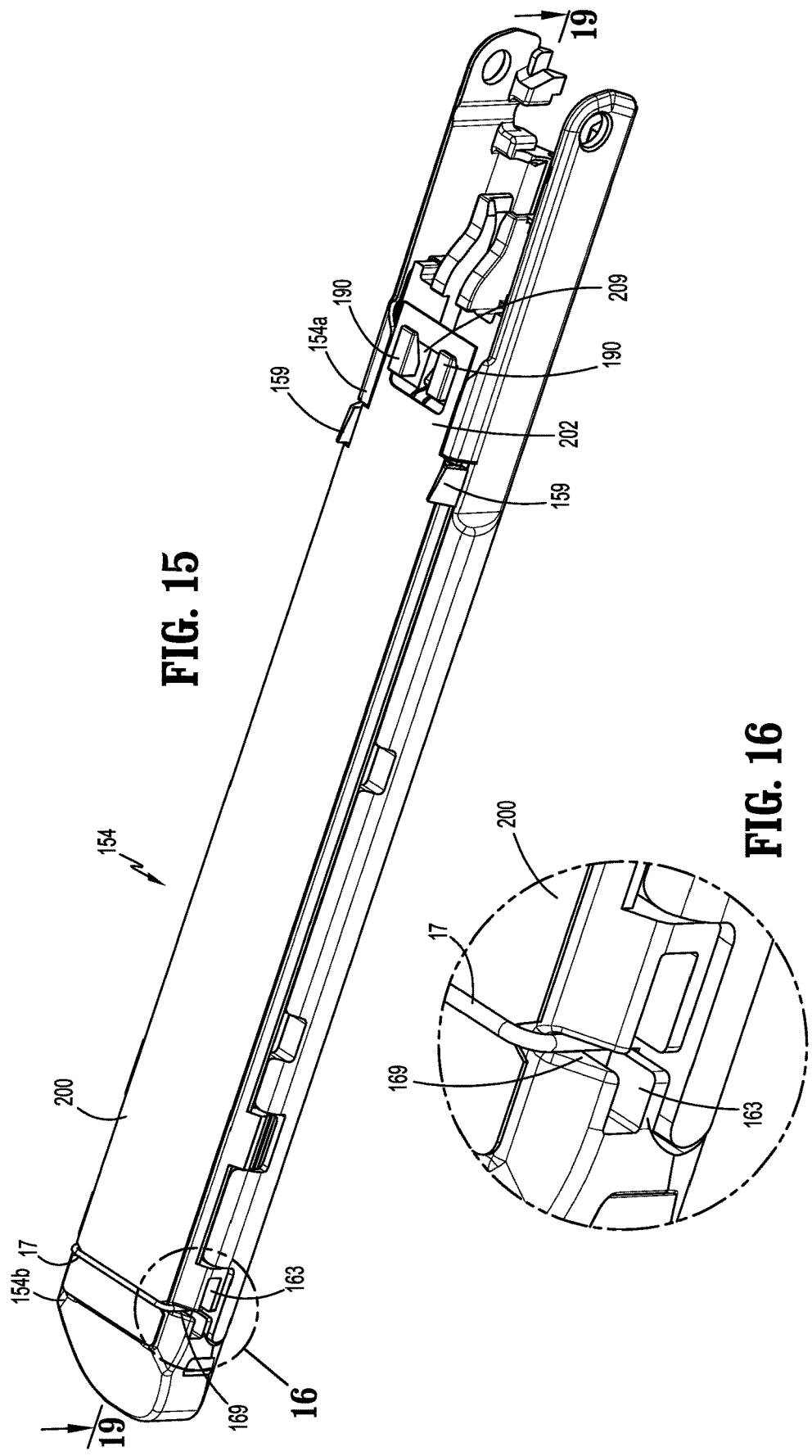

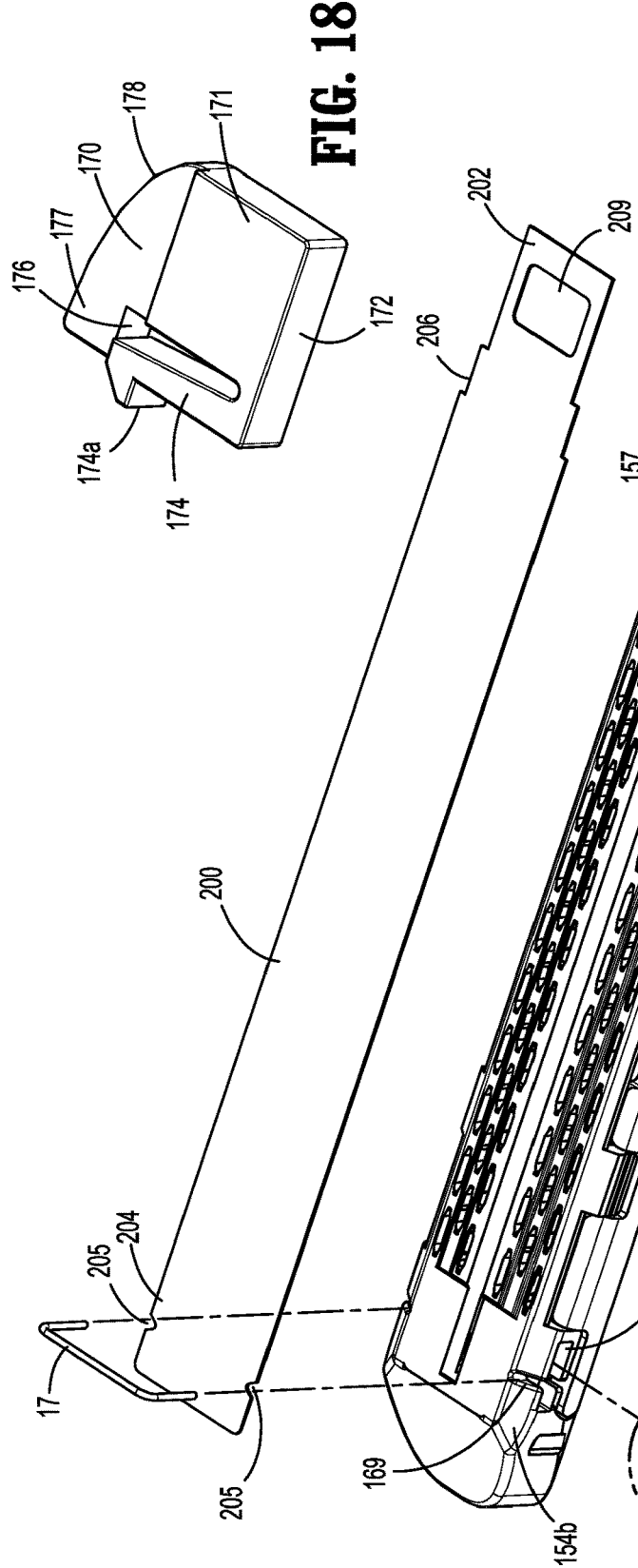
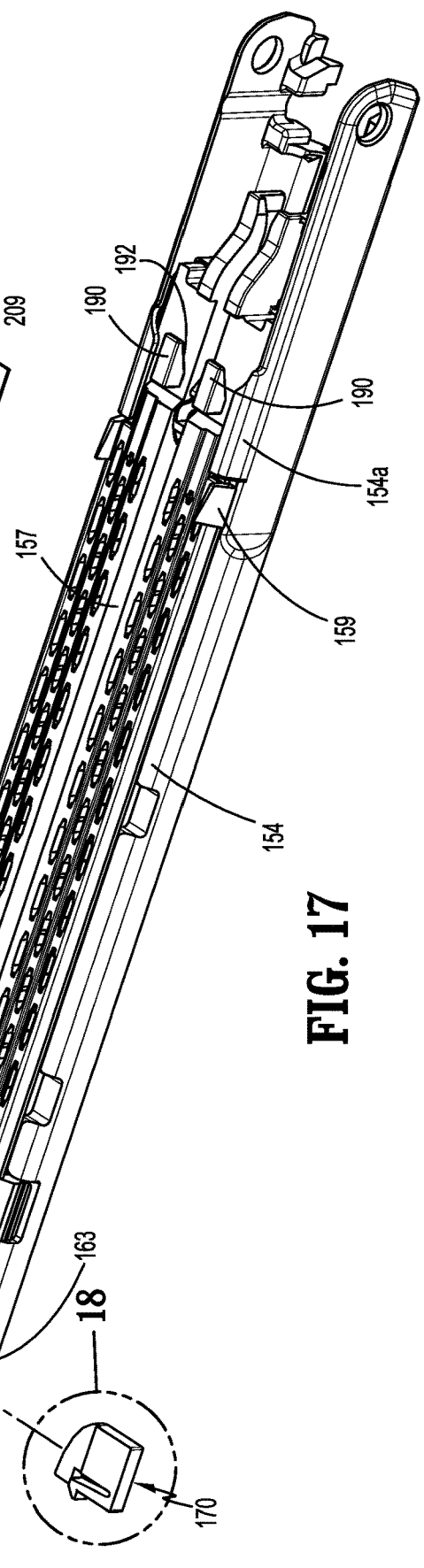
FIG. 18
FIG. 17

SURGICAL STAPLE CARTRIDGE FOR SUPPORTING SURGICAL BUTTRESS MATERIAL

CROSS-REFERENCE TO RELATED APPLICATION(S)

This application is a continuation of U.S. patent application Ser. No. 17/679,162, filed on Feb. 24, 2022 (now U.S. Pat. No. 11,918,218), which is a divisional of U.S. patent application Ser. No. 16/748,899, filed on Jan. 22, 2020 (now U.S. Pat. No. 11,272,937), the entire disclosure of each of which being incorporated by reference herein.

TECHNICAL FIELD

The present application relates to surgical staplers, and more particularly, to a surgical staple cartridge configured to detachably support a surgical buttress material.

BACKGROUND

Surgical staplers are employed by surgeons to sequentially or simultaneously apply one or more rows of fasteners, e.g., staples or two-part fasteners, to body tissue for the purpose of joining segments of body tissue together and/or creating anastomoses. Linear surgical staplers generally include a pair of jaws or finger-like structures between which the body tissue to be joined is placed. When the linear surgical staplers are actuated, or "fired," longitudinally moving firing bars contact staple drive members in one of the jaws. The staple drive members push the surgical staples through the body tissue and into an anvil in the opposite jaw which forms the staples. If body tissue is to be removed or separated, a knife blade can be provided in one of the jaws of the apparatus to cut the body tissue between the lines of staples.

Surgical supports, e.g., meshes or buttress materials, may be used in combination with surgical staplers to bridge, repair, and/or reinforce tissue defects within a patient such as those occurring, for example, in the abdominal wall, chest wall, diaphragm, or musculo-aponeurotic areas of the body. The surgical buttress material reinforces the staple line as well as covers the juncture of the tissues to reduce leakage prior to healing. The surgical buttress material can help promote proper staple formation while reducing twisting/malformation caused by any misalignment of tissue and/or unusual or non-uniform tissue. The surgical buttress material can also provide support to weakened tissue, or help address differences in the thickness of tissues.

Accordingly, new systems and methods that enable easy and efficient attachment and removal of a surgical buttress material to and from the surgical staplers would be desirable.

SUMMARY

In accordance with an embodiment of the present disclosure, an end effector for use with a surgical stapler includes an anvil assembly and a staple cartridge assembly movable relative to the anvil assembly between an approximated position and a spaced apart position. The staple cartridge assembly defines a plurality of retention slots and a cavity. The staple cartridge assembly includes a plurality of staples, a plurality of pushers, an actuation sled, a surgical buttress material, a suture, and an anchoring button. The plurality of staples is disposed in the respective plurality of retention slots. The plurality of pushers is configured to eject the plurality of staples through the respective plurality of retention slots. The actuation sled is configured for movement along a length of the staple cartridge assembly to sequentially engage the plurality of pushers to eject the plurality of staples through the respective plurality of retention slots. The actuation sled includes a first knife blade. The surgical buttress material is configured to be supported on a tissue facing surface of the staple cartridge assembly. The suture includes opposing ends securely attached to opposing lateral sides of the staple cartridge assembly. The anchoring button is configured to be received in the cavity of the staple cartridge assembly such that a portion of the suture is supported in the cavity so as to be severed by the first knife blade of the actuation sled when the actuation sled is advanced distally.

In an embodiment, the staple cartridge assembly may further define opposing lateral grooves configured to securely receive the respective opposing ends of the suture.

In another embodiment, the anchoring button may define opposing peripheral grooves in registration with the respective opposing lateral grooves of the staple cartridge assembly.

In yet another embodiment, the anchoring button may define a notch configured to receive the first knife blade of the actuation sled therethrough.

In still yet another embodiment, the portion of the suture may be disposed orthogonal to a central longitudinal axis defined by the staple cartridge assembly.

In still yet another embodiment, the anchoring button may include an engaging portion defining a transverse groove configured to support the portion of the suture within the cavity.

In an embodiment, the staple cartridge assembly may include opposing lateral guides configured to receive the surgical buttress material therebetween.

In another embodiment, the staple cartridge assembly may further define a central longitudinal slot in communication with the cavity.

In an embodiment, the central longitudinal slot may extend through the cavity.

In another embodiment, the actuation sled may further include a second knife blade configured to extend through the central longitudinal slot to cut the surgical buttress material and tissue in superposed relation with the tissue facing surface of the staple cartridge assembly.

In yet another embodiment, the surgical buttress material may have a distal portion including a cutout in registration with a distal portion of the central longitudinal slot.

In still yet another embodiment, the cavity of the staple cartridge assembly may be defined at a distal portion of the staple cartridge assembly.

In accordance with another embodiment of the present disclosure, an end effector for use with a surgical stapler includes an anvil assembly and a staple cartridge assembly movable relative to the anvil assembly between an approximated position and a spaced apart position. The cartridge assembly defines a plurality of retention slots and a lateral slot. The cartridge assembly includes a plurality of staples, a plurality of pushers, an actuation sled, a surgical buttress material, a suture, and a slider cam. The plurality of staples is disposed in the respective plurality of retention slots. The plurality of pushers is configured to eject the plurality of staples through the respective plurality of retention slots. The actuation sled is configured for movement along a length of the staple cartridge assembly to engage the plurality of pushers to eject the plurality of staples through the respective plurality of retention slots. The surgical buttress material is configured to be supported on a tissue facing surface of the staple cartridge assembly. The suture includes opposing ends securely attached to opposing lateral sides of the staple cartridge assembly. The slider cam is configured to be slidably received in the lateral slot. The slider cam includes an engaging portion configured to engage the actuation sled such that axial displacement of the actuation sled causes lateral movement of the slider cam which in turn releases one end of the opposing ends of the suture from the corresponding lateral groove of the staple cartridge assembly.

In an embodiment, the engaging portion may have an arcuate or tapered profile.

In another embodiment, the slider cam may further include a lateral portion having a planar surface configured to engage the one end of the opposing ends of the suture.

In yet another embodiment, the slider cam may include a body portion including the lateral portion, and a finger flexibly extending distally from the body portion.

In still yet another embodiment, the lateral slot may include a first stop configured to engage a portion of the finger to limit lateral displacement of the slider cam.

In still yet another embodiment, the finger may include a hook portion configured to engage the first stop of the lateral slot.

In an embodiment, the staple cartridge assembly may define a central longitudinal slot extending along a length thereof.

In another embodiment, the lateral slot of the staple cartridge assembly may further include a second stop configured to limit lateral displacement of the slider cam towards the central longitudinal slot.

In an embodiment, the slider cam may be disposed laterally inward of the opposing ends of the suture.

In another embodiment, the surgical buttress material may define opposing notches configured to be in registration with the respective opposing lateral grooves of the staple cartridge assembly.

In yet another embodiment, the staple cartridge assembly may include opposing lateral guides configured to receive the surgical buttress material therebetween.

In still yet another embodiment, the surgical buttress material may include stepped portions configured to engage the respective opposing lateral guides.

In still yet another embodiment, the staple cartridge assembly may further include a hook member extending from the tissue facing surface.

In an embodiment, the surgical buttress material may define a cutout.

In another embodiment, the hook member may be configured to be received through the cutout of the surgical buttress material to secure the surgical buttress material to the staple cartridge assembly.

In yet another embodiment, the actuation sled may include a knife blade configured to extend through the central longitudinal slot to cut the surgical buttress material and tissue in superposed relation with the tissue facing surface of the staple cartridge assembly.

In still yet another embodiment, the opposing ends of the suture may be frictionally secured within the respective opposing lateral grooves of the staple cartridge assembly.

In accordance with yet another embodiment of the present disclosure, an end effector for use with a surgical stapler includes an anvil assembly and a staple cartridge assembly movable relative to the anvil assembly between an approximated position and a spaced apart position. The cartridge assembly defines a plurality of retention slots and a lifting slot. The cartridge assembly includes a plurality of staples, a plurality of pushers, an actuation sled, a surgical buttress material, a suture, and a lifting member. The plurality of staples is disposed within the respective plurality of retention slots. The plurality of pushers is configured to eject the plurality of staples through the respective plurality of retention slots. The actuation sled is configured for movement along a length of the staple cartridge assembly to engage the plurality of pushers to eject the plurality of staples through the respective plurality of retention slots. The surgical buttress material is configured to be supported on a tissue facing surface of the staple cartridge assembly. The suture includes opposing ends securely attached to opposing lateral sides of the staple cartridge assembly to detachably secure the surgical buttress material to the tissue facing surface. The lifting member is configured to extend through the lifting slot to urge the suture away from the surgical buttress material to release the surgical buttress material from the staple cartridge assembly.

In an embodiment, the lifting member may be coupled to one pusher of the plurality of pushers.

In another embodiment, the lifting member may be coupled to a distal-most pusher of the plurality of pushers.

In yet another embodiment, the staple cartridge assembly may define opposing lateral grooves configured to secure respective opposing ends of the suture.

In still yet another embodiment, one groove of the opposing lateral grooves may be adjacent the lifting slot such that a portion of the suture extends over the lifting slot.

In an embodiment, the suture may be flexible.

In another embodiment, the staple cartridge assembly may include opposing lateral guides configured to receive the surgical buttress material therebetween.

In yet another embodiment, the surgical buttress material may define a cutout.

In still yet another embodiment, the staple cartridge assembly may include a hook member extending from the tissue facing surface thereof. The hook member may be configured to be received through the cutout of the surgical buttress material to secure the surgical buttress material to the staple cartridge assembly.

BRIEF DESCRIPTION OF THE DRAWINGS

The above and other aspects, features, and advantages of the present disclosure will be apparent in light of the following detailed description when taken in conjunction with the accompanying drawings, which are incorporated in and constitute a part of this specification, wherein:

FIG. 1 is a perspective view of a surgical stapler having a surgical buttress material mounted thereon in accordance with an embodiment of the present disclosure;

FIG. 2 is a perspective view of an end effector of the surgical stapler of FIG. 1;

FIG. 15 is a perspective view of a staple cartridge assembly for use with the surgical stapler of FIG. 1 in accordance with another embodiment of the present disclosure;

FIG. 16 is an enlarged view of the indicated area of detail of FIG. 15;

FIG. 17 is a perspective view of the staple cartridge assembly of FIG. 15 with the surgical buttress material separated;

FIG. 18 is an enlarged view of the indicated area of detail of FIG. 17, illustrating a slider cam of the staple cartridge assembly of FIG. 15;

DETAILED DESCRIPTION

Figure 3:
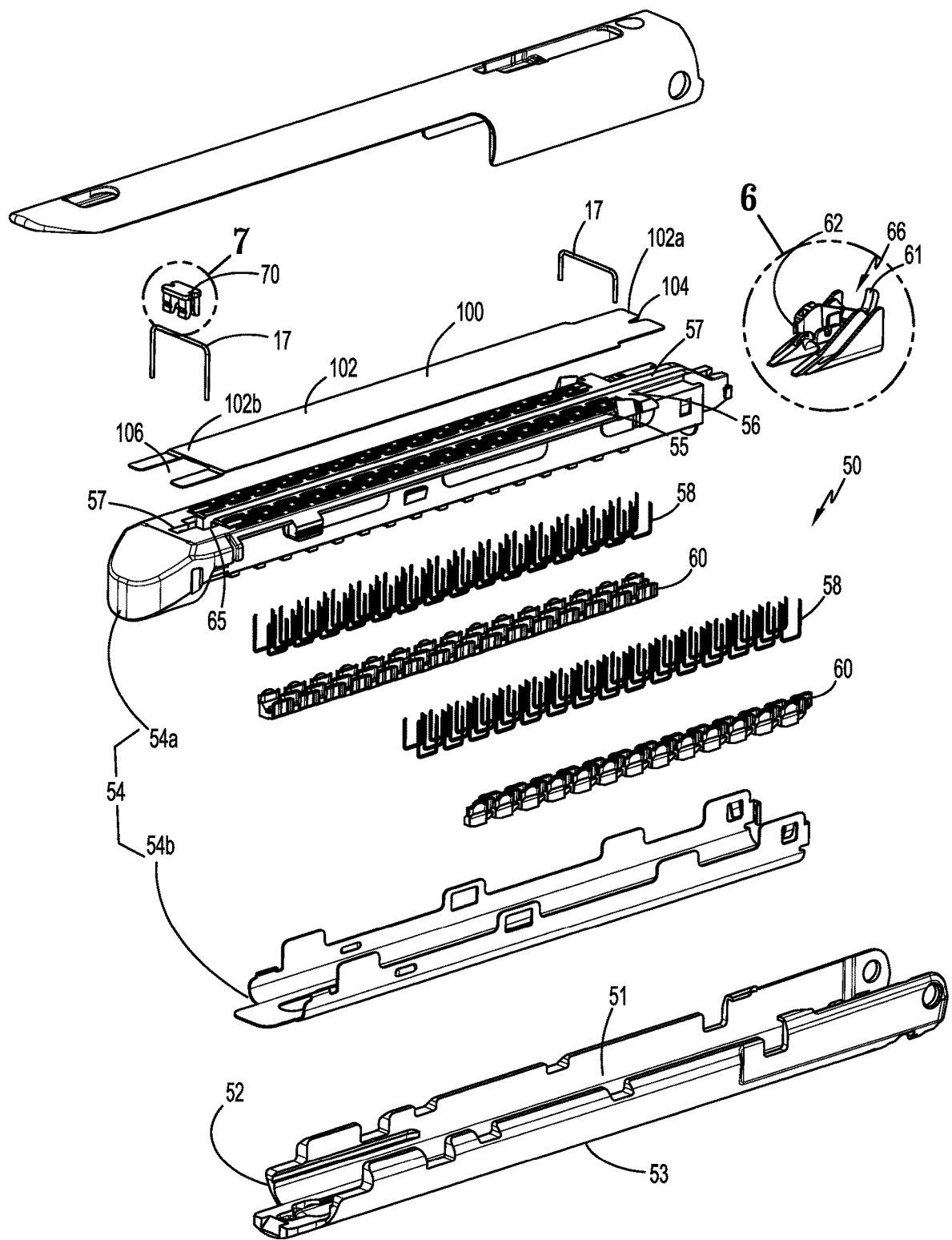
FIG. 3 is an exploded, perspective view of a tool portion of the end effector of FIG. 1 with parts separated.

Embodiments of the present disclosure will now be described in detail with reference to the drawing figures wherein like reference numerals identify similar or identical elements. Throughout this description, the term "proximal" refers to a portion of a structure, or component thereof, that is closer to a user, and the term "distal" refers to a portion of the structure, or component thereof, that is farther from the user. Directional reference terms, such as "top," "bottom," "side," and the like, are used to case description of the embodiments and are not intended to have any limiting effect on the ultimate orientation of a structure or any part thereof. In the following description, well-known functions or constructions are not described in detail to avoid obscuring the present disclosure in unnecessary detail.

Referring now to FIGS. 1-3, an exemplary surgical stapler 1 in the form of a linear surgical stapler is shown for use in stapling tissue and applying a surgical buttress material 100 to the tissue. The surgical stapler 1 generally includes a handle assembly 10, an elongate tubular body portion 20 extending distally from the handle assembly 10, and an end effector 30 extending distally from the elongate tubular body portion 20. The end effector 30 includes an anvil assembly 40 and a staple cartridge assembly 50. The end effector 30 may be permanently affixed or detachably coupled to the elongate tubular body portion 20 and thus, replaceable with a new end effector 30. The anvil assembly 40 and/or the staple cartridge assembly 50 may be pivotable relative to each other such that the anvil and/or staple cartridge assemblies 40, 50 is movable between an open position, in which the anvil and staple cartridge assemblies 40, 50 are spaced apart with respect to each other, and an approximated position, in which the anvil and staple cartridge assemblies 40, 50 are substantially adjacent each other. The handle assembly 10 includes an actuation button 12 configured to actuate, e.g., an electrical motor (not shown), operatively associated with an actuation sled 66 to eject staples 58 out of the staple cartridge assembly 50, and open and close buttons 14, 16 configured to actuate, e.g., an electrical motor (not shown), operatively associated with the anvil and/or staple cartridge assemblies 40, 50 to transition the anvil and/or staple cartridge assemblies 40, 50 between the open and approximated positions.

For a detailed description of the structure and function of exemplary surgical staplers, reference may be made to U.S. Pat. Nos. 8,256,656, 7,819,896, and 7,128,253, the entire content of each of which is incorporated herein by reference. It should be appreciated that principles of the present disclosure are equally applicable to surgical staplers having other configurations such as, for example, the types described in U.S. Pat. Nos. 7,334,717, 5,964,394, and 5,915,616, the entire content of each of which is incorporated herein by reference. Accordingly, it should be understood that a variety of surgical staplers may be utilized.

With reference to FIG. 2, the anvil assembly 40 includes an anvil plate (not shown) having a central longitudinal slot formed therein, and a cover plate 44 secured over the anvil plate such that the cover plate 44 defines a top or outwardly facing surface 46 of the anvil assembly 40. The anvil plate may include a plurality of staple forming pockets/cavities (not shown) defined in an inwardly or tissue facing surface (not shown) thereof.

With reference to FIG. 3, the staple cartridge assembly 50 includes a cartridge carrier 52 defining an elongated support channel 51 configured and dimensioned to selectively receive a staple cartridge 54 therein. The cartridge carrier 52 also defines a bottom or outwardly facing surface 53 of the staple cartridge assembly 50. The staple cartridge 54 is removable and replaceable in the cartridge carrier 52. The staple cartridge 54 includes a body portion 54a and a cover

54*b*. The body portion 54*a* defines staple pockets or retention slots 55 for receiving a plurality of fasteners or staples 58 and staple pushers 60 therein. The staples 58 are of a conventional type and include a backspan having a pair of legs extending from the backspan. The legs terminate in tissue penetrating tips. The staple pushers 60 are located within respective staple pockets 55 and are positioned between the staples 58 and the path of the actuation sled 66. A central longitudinal slot 57 is defined along a length of the staple cartridge 54 for passage of a first knife blade 61 of the actuation sled 66 therethrough.

Figure 4:
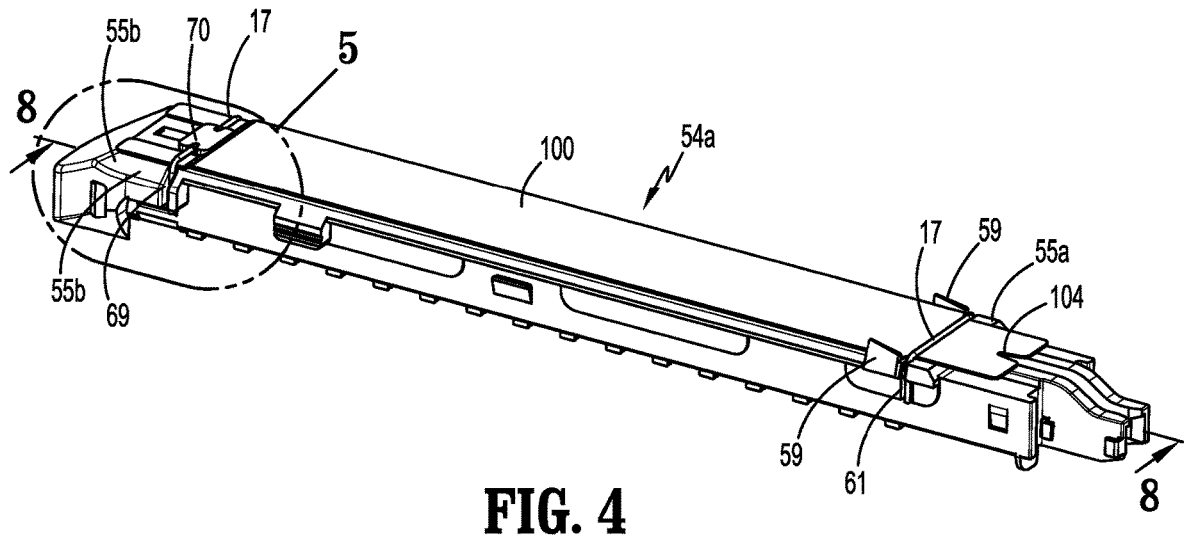
FIG. 4 is a perspective view of a staple cartridge assembly of the end effector of FIG. 1, illustrating the surgical buttress material detachably secured thereon.
Figure 5:
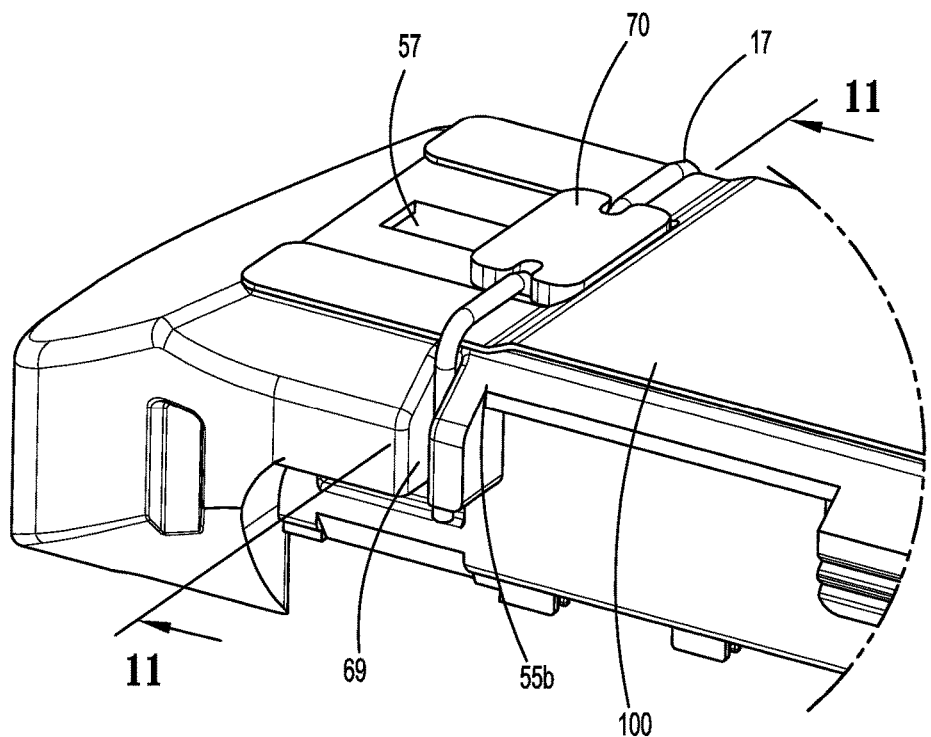
FIG. 5 is an enlarged view of the indicated area of detail of FIG. 4.

With reference to FIGS. 4 and 5, a cavity 65 (FIG. 3) is defined adjacent a distal portion of the central longitudinal slot 57. The cavity 65 is configured to receive an anchoring button 70 to support a suture 17 securing the surgical buttress material 100 on the staple cartridge 54, as will be discussed below. Proximal and distal portions 55*a*, 55*b* of the body portion 54*a* of the staple cartridge 54 are configured to secure the respective sutures 17 thereto, in order to detachably secure the surgical buttress material 100 to the tissue facing surface 56 (FIG. 3) of the body portion 54*a*. To this end, the proximal portion 55*a* of the body portion 54*a* defines lateral grooves 69 configured to securely receive respective end portions of the suture 17 therein. For example, the end portions of the suture 17 may be secured to the lateral grooves 69 through friction fit or through use of an adhesive. Alternatively, the suture 17 may be ultrasonically welded to the lateral groove 69. In addition, the proximal portion 55*a* of the body portion 54*a* includes a pair of lateral guides 59 extending from the tissue facing surface 56 (FIG. 3). The surgical buttress material 100 is received between the lateral guides 59. In this manner, the suture 17 in conjunction with the pair of lateral guides 59 secures the surgical buttress material 100 to the proximal portion 55*a* of the body portion 54*a*.

With continued reference to FIGS. 4 and 5, the surgical buttress material 100 is further secured to the staple cartridge 54 by another suture 17 in the distal portion 55*b* of the body portion 54*b*. While the present disclosure discloses two sutures 17 to secure the respective proximal and distal portions 102*a*, 102*b* of the surgical buttress material 100 to the body portion 54*b*, it is contemplated that any number of sutures 17 may be utilized to effect securement of the surgical buttress material 100 to the staple cartridge 54. The distal portion 55*b* of the body portion 54*b* of the staple cartridge 54 defines opposing lateral grooves 69 (only one shown) configured to securely receive respective end portions of the suture 17. The suture 17 secured to the opposing lateral grooves 69 is used to secure the distal end 102*b* of the surgical buttress material 100 to the distal portion 55*b* of the staple cartridge 54.

With reference now to FIGS. 6-10, in order to enhance securement and detachability of the surgical buttress material 100 to and from the staple cartridge 54, the anchoring button 70 is placed in the cavity 65 of the body portion 54*a* of staple cartridge 54. The cavity 65 is defined in the distal portion 55*b* of the staple cartridge 54. In particular, the central longitudinal slot 57 extends through the cavity 65. The anchoring button 70 includes first and second fingers 72, 74 configured to flex relative to each other. The anchoring button 70 includes an engaging portion 75 disposed between the first and second fingers 72, 74 to support a portion of the suture 17 thereon. The anchoring button 70 defines opposing peripheral grooves 76*a*, 76*b* configured to receive the suture 17 therein. Further, the anchoring button 70 defines a notch 73 extending through the first and second fingers 72, 74. The notch 73 is configured to receive the second knife blade 62 of the actuation sled 66 therethrough. Under such a configuration, when the actuation sled 66 is advanced, the second knife blade 62 of the actuation sled 66 extends through the notch 73 and severs a portion of the suture 17 extending across the notch 73. At least one finger of the first and second fingers 72, 74 of the anchoring button 70 further defines cutouts 77 configured to engage a stop 67 (FIG. 9) extending inwardly into the cavity 65 of the staple cartridge 54. Under such a configuration, when the anchoring button 70 is pushed into the cavity 65 in the direction of an arrow "L" (FIG. 9), the stop 67 engages the cutout 77, and the stop 67 inhibits the anchoring button 70 from pulling back out in a direction opposite of the arrow "L" such that the anchoring button 70 remains in the cavity 65 once placed therein.

Figure 11:
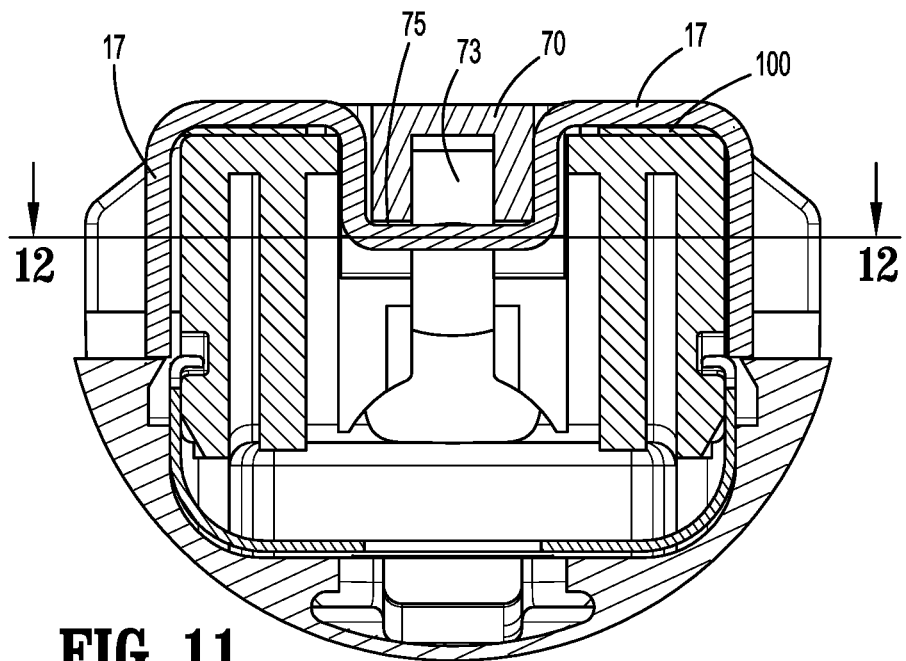
FIG. 11 is a cross-sectional view of the staple cartridge assembly of FIG. 5 taken along section line 11-11 of FIG. 5.

With reference to FIG. 11, opposing ends of the suture 17 are secured to the respective lateral grooves 69 (FIG. 5) of the distal portion 55*b* of the staple cartridge 54, and a portion of the suture 17 is supported within the cavity 65 of the staple cartridge 54 by the anchoring button 70. Under such a configuration, a portion of the suture 17 extends between the first and second fingers 72, 74 and across the notch 73 (FIG. 6) to be severed by the second knife blade 62 of the actuation sled 66 advancing through the notch 73.

Figure 6:
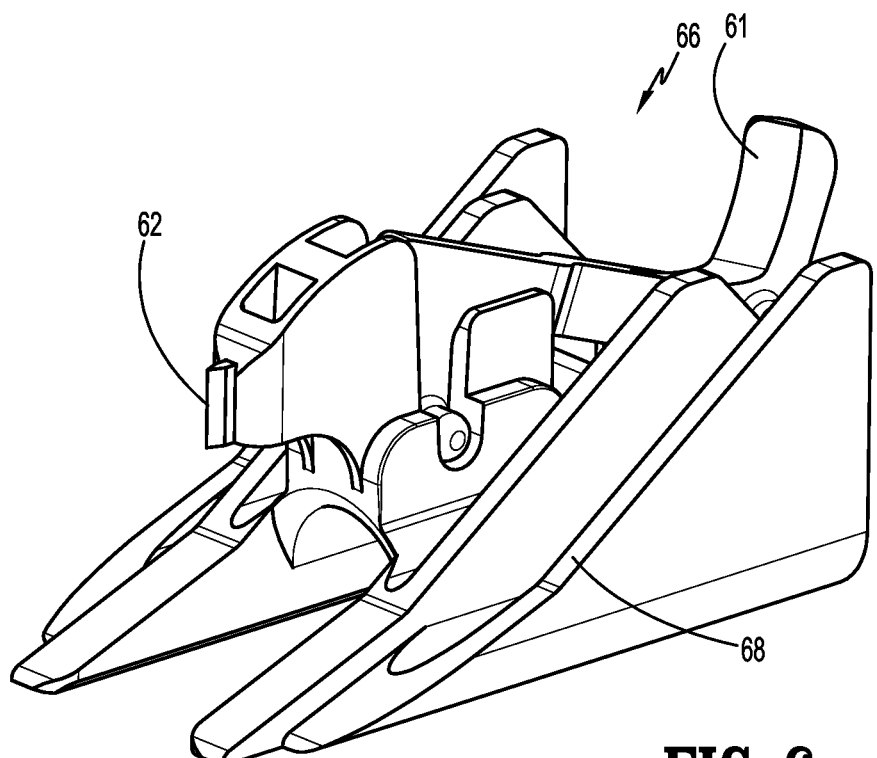
FIG. 6 is an enlarged view of the indicated area of detail of FIG. 3 illustrating an actuation sled of the staple cartridge assembly of FIG. 4.
Figure 7:
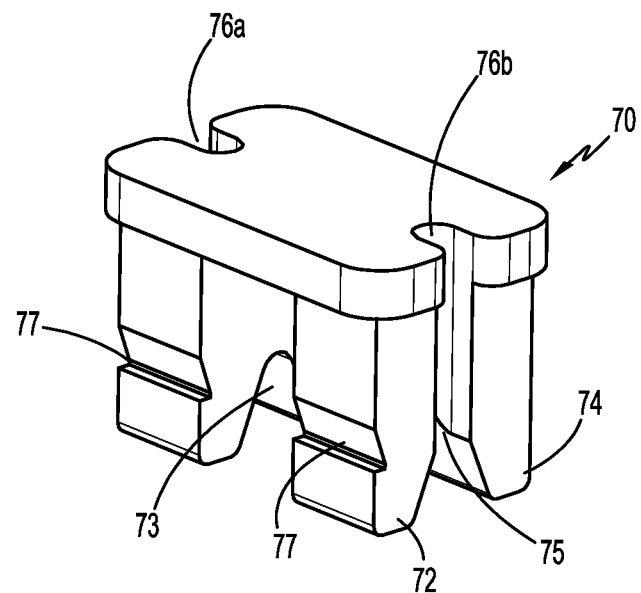
FIG. 7 is an enlarged view of the indicated area of detail of FIG. 3 illustrating an anchoring button of the staple cartridge assembly of FIG. 4.
Figure 8:
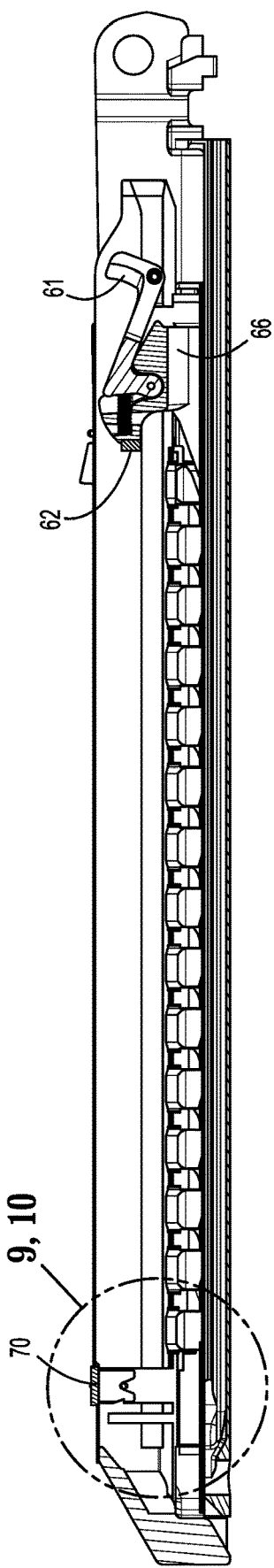
FIG. 8 is a cross-sectional view of the staple cartridge assembly of FIG. 4, taken along section line 8-8 of FIG. 4.
Figure 10:
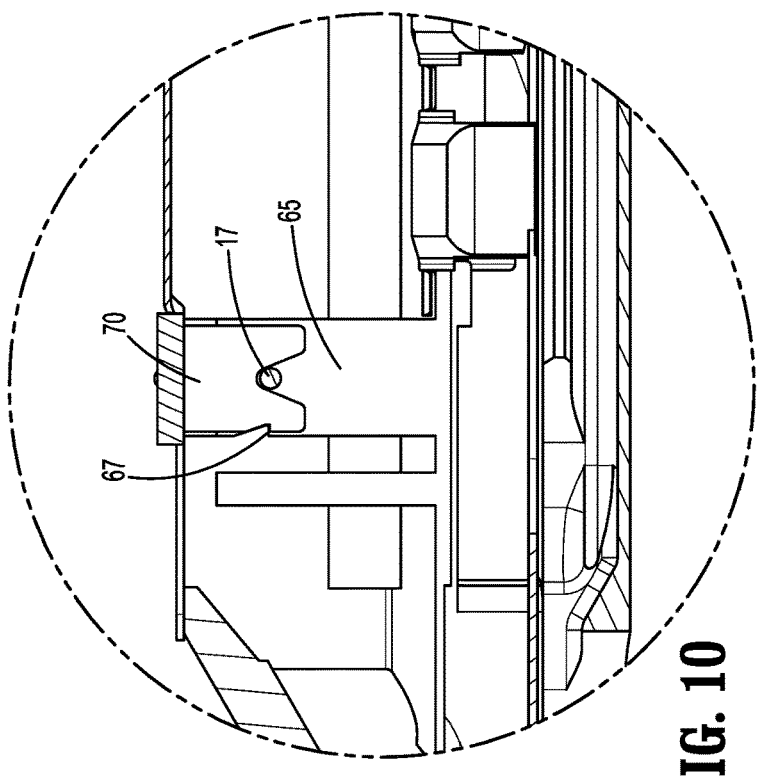
FIGS. 9 and 10 are enlarged views of the indicated area of detail of FIG. 8, illustrating placement of the anchoring button with the staple cartridge assembly of FIG. 8.
Figure 9:
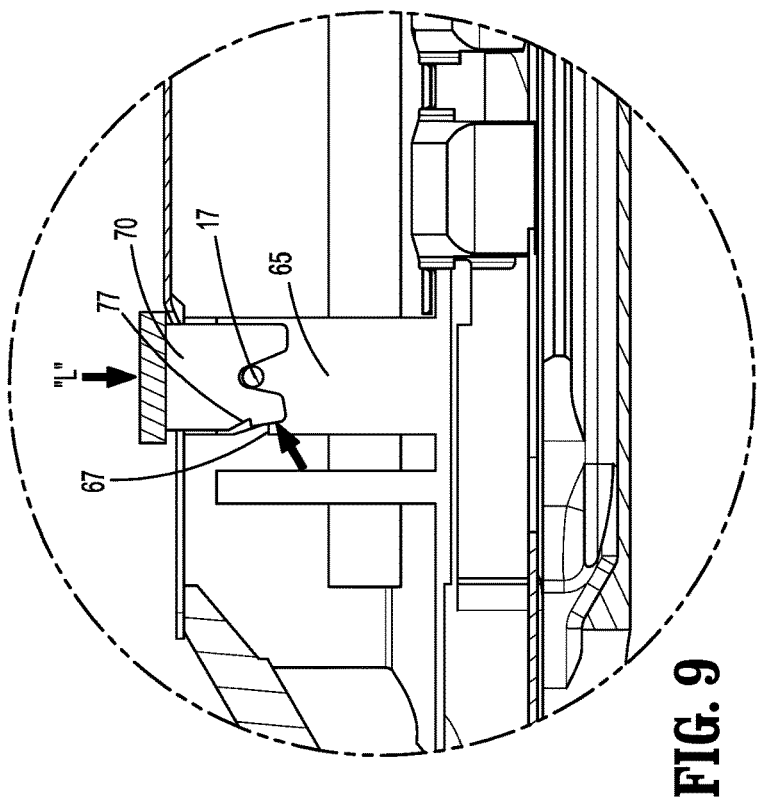

With brief reference back to FIG. 6, the actuation sled 66 includes a cam wedge 68 configured to engage the staple pushers 60 (FIG. 3) in sequence, a first knife blade 61 configured to be received through the central longitudinal slot 57 to cut tissue and the surgical buttress material 100, and a second knife blade 62 configured to be received through the notch 73 (FIG. 7) of the anchoring button 70. During operation of the surgical stapler 1, the actuation sled 66 translates through the staple cartridge 54 to advance the cam wedge 68 into sequential contact with the staple pushers 60, to cause the staple pushers 60 to move vertically within the staple pockets 55 and eject the staples 58 out of the staple pockets 55 towards the tissue facing surface of the anvil plate (not shown) of the anvil assembly 40. Further, the second knife blade 62 is configured to sever the suture 17 positioned against the anchoring button 70, as will be discussed below.

With reference to FIGS. 11, initially, the staple cartridge 54 is loaded in the cartridge carrier 52 (FIG. 3). The surgical buttress material 100 may be detachably secured to the staple cartridge 54 at any time before or after the loading of the staple cartridge 54 in the cartridge carrier 52. The surgical buttress material 100 is fabricated from biocompatible materials which are bioabsorbable or non-absorbable, natural or synthetic. It should be understood that any combination of natural, synthetic, bioabsorbable, and/or non-bioabsorbable materials may be used to form the surgical buttress material 100. The surgical buttress material 100 may be biodegradable (e.g., formed from bioabsorbable and bioresorable materials) such that the surgical buttress material 100 decomposes or is broken down (physically or chemically) under physiological conditions in the body, and the degradation products are excretable or absorbable by the body. Components or portions of the surgical buttress material 100 may be formed from the same material or different materials. The entire surgical buttress material 100 may be formed (e.g., cut) from a single sheet of material, or may be formed from a plurality of sheets of material, that are fabricated from the same or different materials, and attached to one another by, for example, welding, using adhesives, tying sutures, etc.

In embodiments, at least a portion of the surgical buttress material 100 is made from biodegradable materials selected from the following group: natural collagenous materials, cat gut, and synthetic resins including those derived from alkylene carbonates, trimethylene carbonate, tetramethylene carbonate, caprolactone, valerolactone, dioxanone, polyanhydrides, polyesters, polyacrylates, polymethylmethacrylates, polyurethanes, glycolic acid, lactic acid, glycolide, lactide, polyhydroxy butyrates, polyorthoester, polyhydroxy alkanoates, homopolymers thereof, and copolymers thereof. In embodiments, at least a portion of the surgical buttress material 100 is made from non-biodegradable materials selected from the following group: polyolefins, polyethylene, polydimethylsiloxane, polypropylene, copolymers of polyethylene and polypropylene, blends of polyethylene and polypropylene, ultra-high molecular weight polyethylene, polyamides, polyesters, polyethylene terephthalate, polytetrafluoroethylene, polyether-esters, polybutester, polytetramethylene ether glycol, 1,4-butanediol, and polyurethanes.

The surgical buttress material 100 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical buttress material 100, or portions thereof, may be a non-woven structure formed by melt-blown or melt-spun methods, a mesh material, a braided material, and/or a molded or extruded sheet. The surgical buttress material 100, or portions thereof, may be a single porous or non-porous layer, or include a plurality of layers including any combination of porous and/or non-porous layers.

In use, the loaded surgical stapler 1 is introduced to a surgical site through, e.g., a trocar or other access device. Tissue may be grasped between the anvil assembly 40 and the staple cartridge assembly 50 by pressing the close button 16 of the handle assembly 10. Once the anvil and staple cartridge assemblies 40, 50 are clamped onto tissue, the clinician may press the actuation button 12 to start the stapling process thereby advancing the actuation sled 66. As the actuation sled 66 advances distally and urges the staple pushers 60 upwardly against the backspans of the staples 58, the staples 58 are ejected out of the staple pockets 55 and through the surgical buttress material 100 as well as the captured tissue, thereby stapling the surgical buttress material 100 to the tissue. The tissue penetrating tips of the staples 58 are bent within the staple clinching pockets in the anvil assembly 40 to thereby secure the surgical buttress material 100 mounted on the tissue facing surface 56 against tissue.

Upon actuation of the surgical stapler 1, the first knife blade 61 associated with the surgical stapler 1 and carried by the actuation sled 66, enters the notch 104 of the surgical buttress material 100 and severs tissue, as well as the surgical buttress material 100 on tissue, between the rows of now clinched staples. The resulting tissue is divided and stapled with the staples 58.

Figure 12:
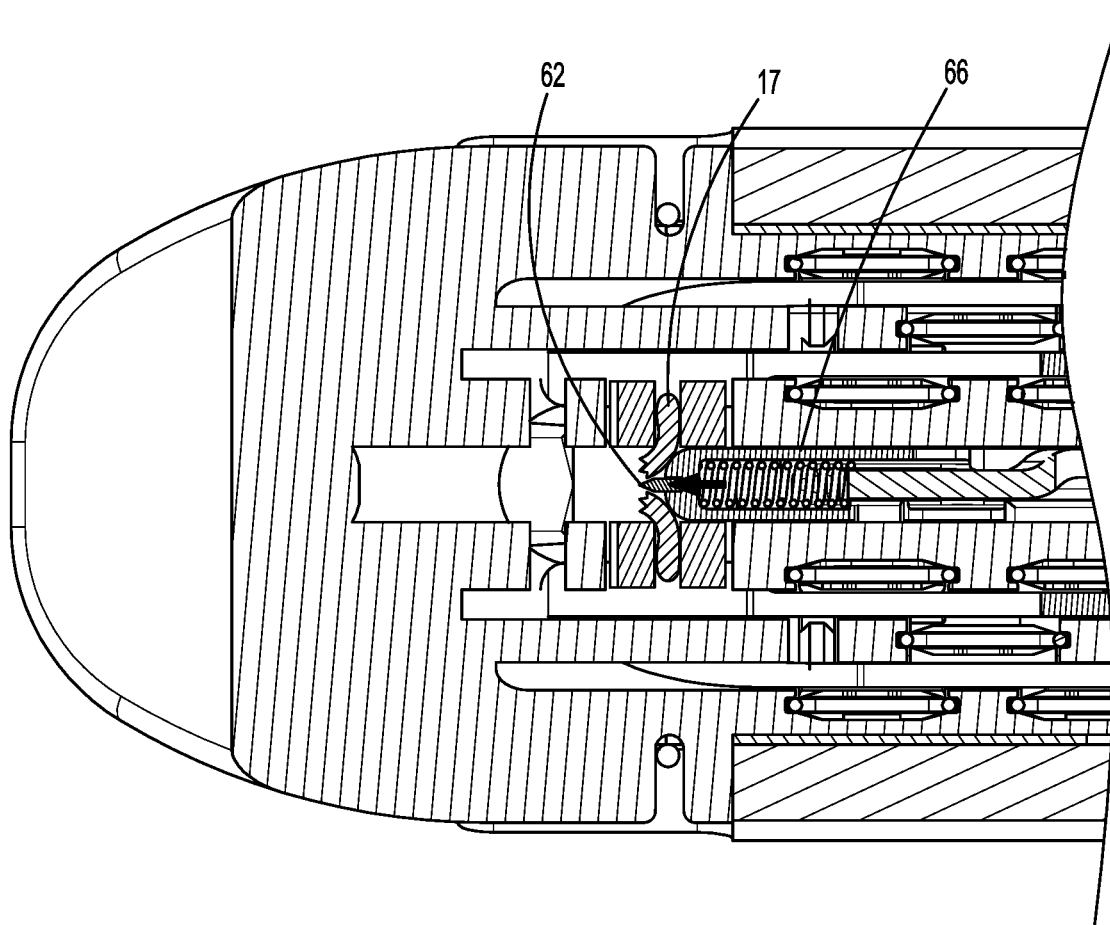
FIG. 12 is a cross-sectional view of the staple cartridge assembly of FIG. 11 taken along section line 12-12 of FIG. 11, illustrating severing of the suture.
Figure 13:
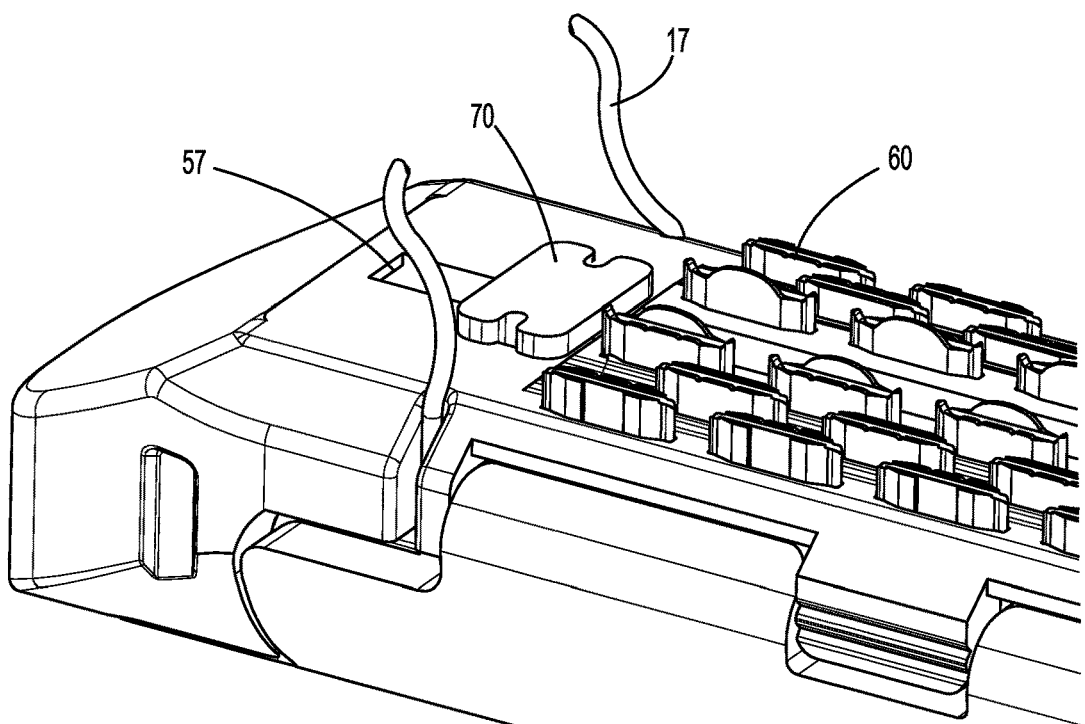
FIG. 13 is a partial perspective view of the staple cartridge assembly of FIG. 8, illustrating severing of the suture.
Figure 14:
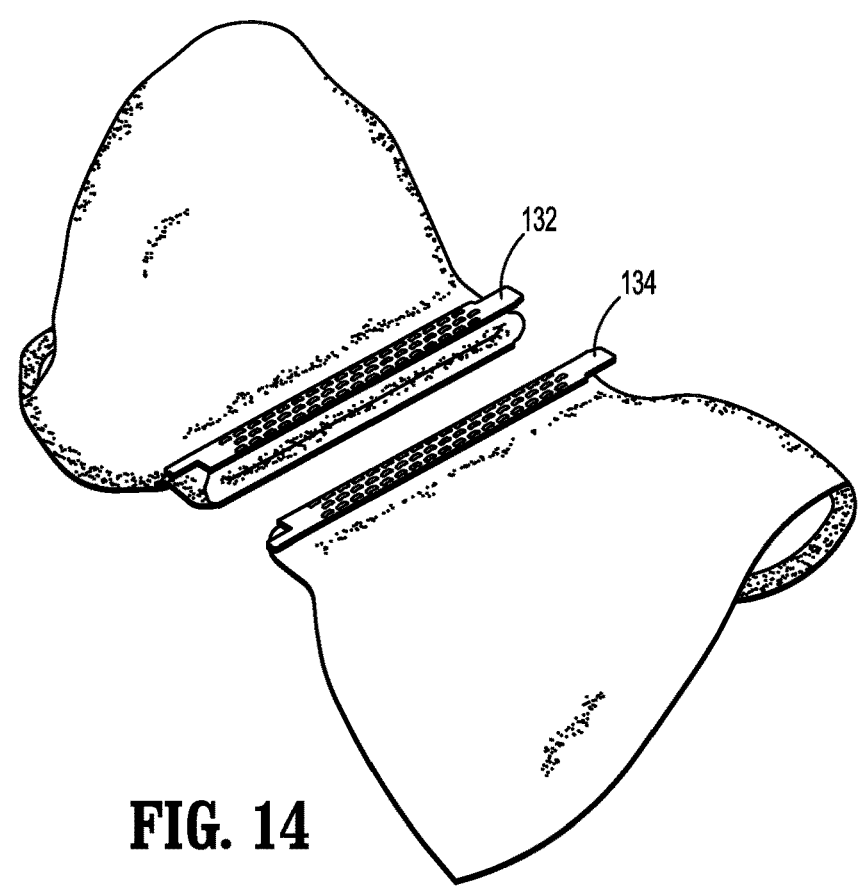
FIG. 14 is a perspective view of tissue stapled and cut by the surgical stapler of FIG. 1.

With reference to FIGS. 12-14, as the actuation sled 66 is further advanced, the first knife blade 61 cuts through the suture 17 securing the surgical buttress material 100 to the proximal portion 55a of the staple cartridge 54. As the actuation sled 66 reaches the distal portion 55b of the staple cartridge 54, the second knife blade 62 of the actuation sled 66 extends through the notch 73 of the anchoring button 70 and severs a portion of the suture 17 extending therein such that the suture 17 securing surgical buttress material 100 to the distal portion 55b of the staple cartridge 54 is severed. In this manner, the surgical buttress material 100 is detachable from the staple cartridge 54 and is split into first and second portions 132, 134. At this time, the clinician may move the end effector 30 and/or actuation sled 66 proximally in order to detach the surgical buttress material 100 stapled to tissue, from the end effector 30. In this manner, the surgical buttress materials 100 may be stapled to tissue thereby sealing and reinforcing the staple lines created by the staples.

The spent staple cartridge 54 is then removed and a new staple cartridge 54 and a new surgical buttress material 100 can be loaded onto the staple carrier 52. A reload with a removable and replaceable staple cartridge is disclosed in U.S. Pat. No. 9,016,539, the disclosure of which is hereby incorporated by reference herein.

With reference to FIGS. 15-17, another embodiment of a staple cartridge for use with the surgical stapler (FIG. 1) is shown as a staple cartridge 154. Parts of the staple cartridge 154 substantially similar to the parts of the staple cartridge 54 (FIG. 3) will not be described herein to avoid obscuring the present disclosure in unnecessary detail. The staple cartridge 154 may be detachably secured to the cartridge carrier 52 (FIG. 1) by, e.g., snap fit or interference fit. The staple cartridge 154 is configured to detachably secure a surgical buttress material 200 thereto. In particular, a proximal portion 154a of the staple cartridge 154 includes opposing lateral guides 159 configured to receive the surgical buttress material 200 therebetween and hook portions 190 configured to anchor a proximal portion 202 of the surgical buttress material 200, as will be discussed below. Further, a distal portion 154b of the staple cartridge 154 defines opposing lateral grooves 169 to secure respective end portions of the suture 17 therein, and a slot 163 configured to receive a slider cam 170 therein in order to detach the surgical buttress material 200 from the staple cartridge 154, as will be described hereinbelow.

The surgical buttress material 200 includes a proximal portion 202 including a stepped portion 206 configured to engage the lateral guides 159 of the staple cartridge 154 and defines a cavity 209 configured to engage and receive the hook portions 190 of the staple cartridge 154. The hook portions 190 may include tapered portions 192 configured to enhance securement of the surgical buttress material 200 with the staple cartridge 154. The distal portion 204 of the surgical buttress material 200 defines opposing lateral notches 205 configured to facilitate engagement with the suture 17. The distal portion 154b of the staple cartridge 154 defines lateral grooves 169 configured to secure respective end portions of the suture 17. In addition, the distal portion 154b of the staple cartridge 154 further defines a slot 163 dimensioned to receive the slider cam 170 slidably received therein.

Figure 19:
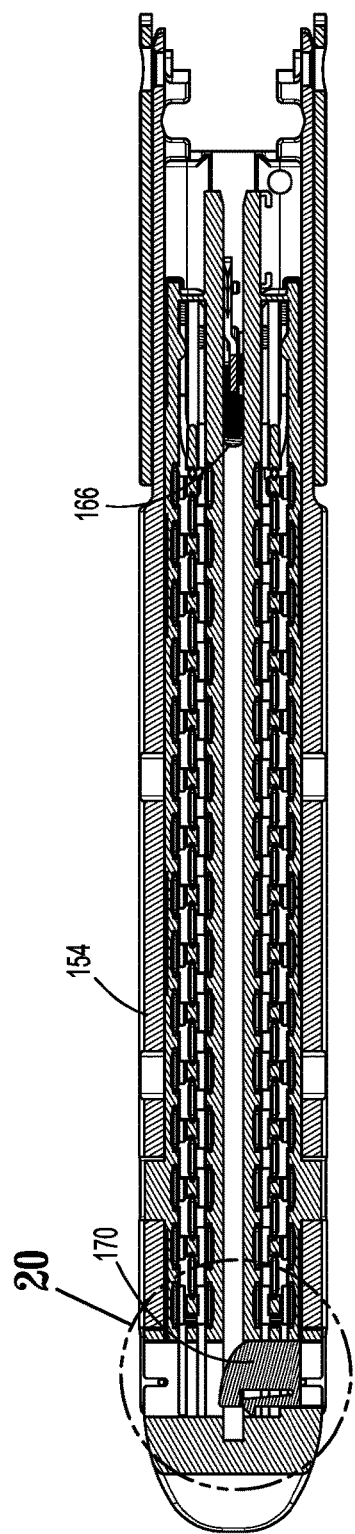
FIG. 19 is a cross-sectional view of the staple cartridge assembly of FIG. 15 taken along section line 19-19 of FIG. 15.
Figure 20:
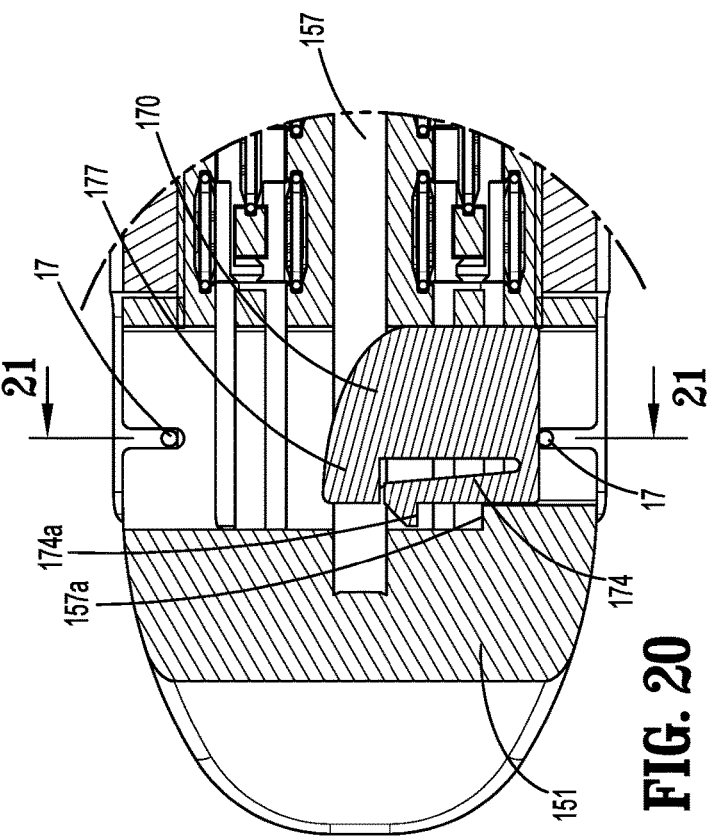
FIG. 20 is an enlarged view of the indicated area of detail of FIG. 19.

With respect to FIGS. 19 and 20, the slider cam 170 is transversely slidable within the slot 163. With particular reference to FIG. 18, the slider cam 170 includes a main body 171 having an engaging surface 172 configured to engage a portion of the suture 17 secured to the corresponding lateral groove 169 in order to disengage the suture 17 from the corresponding lateral groove 169. The slider cam 170 further includes an inner portion 177 extending inwardly from the main body 171, and a finger 174 extending distally from the main body 171. The inner portion 177 has an arcuate surface or a tapered surface 178 configured to engage a portion of the actuation sled 166. The finger 174 is spaced apart from the main body 171 such that the finger 174 is configured to flex towards and away from the main body 171. In an embodiment, the finger 174 is biased away from the main body 171 such that as the slider cam 170 is moved laterally outward, a hook portion 174a of the finger 174 engages an outer stop 157a of a support member 151 (FIG.

20) of the staple cartridge 154 to limit lateral displacement of the slider cam 170. In this manner, the slider cam 170 is movable laterally outwards by a predetermined amount. For example, the slider cam 170 may be displaced laterally outwards by a predetermined amount to displace the suture 17 out of the corresponding lateral groove 169 of the staple cartridge 154.

Figure 21:
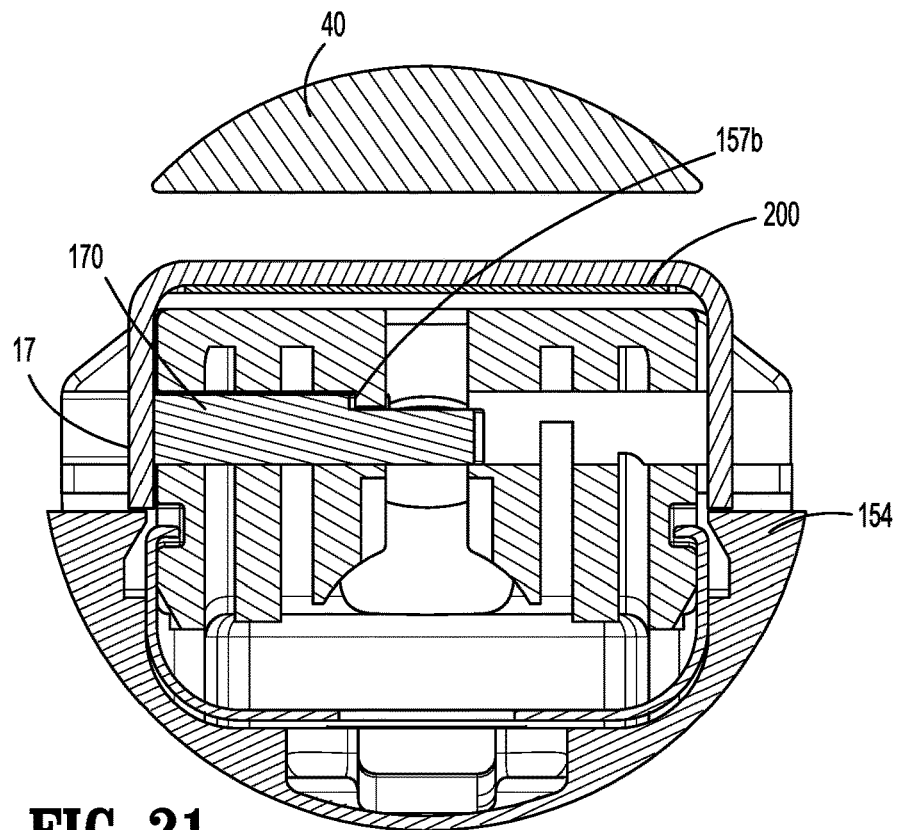
FIG. 21 is cross-sectional view of the surgical cartridge assembly of FIG. 20 taken along section line 21-21 of FIG. 20.
Figure 22:
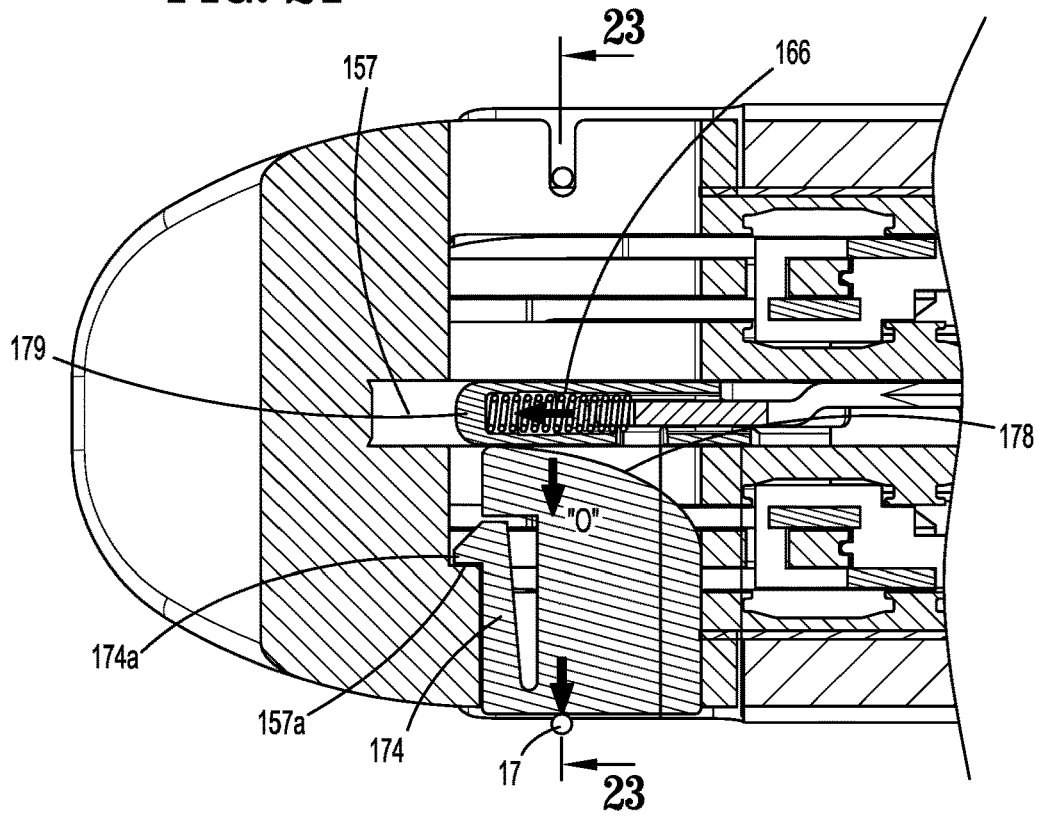
FIG. 22 is a partial cross-sectional view of the surgical cartridge assembly of FIG. 19 illustrating a slider cam in a laterally displaced position.
Figure 23:
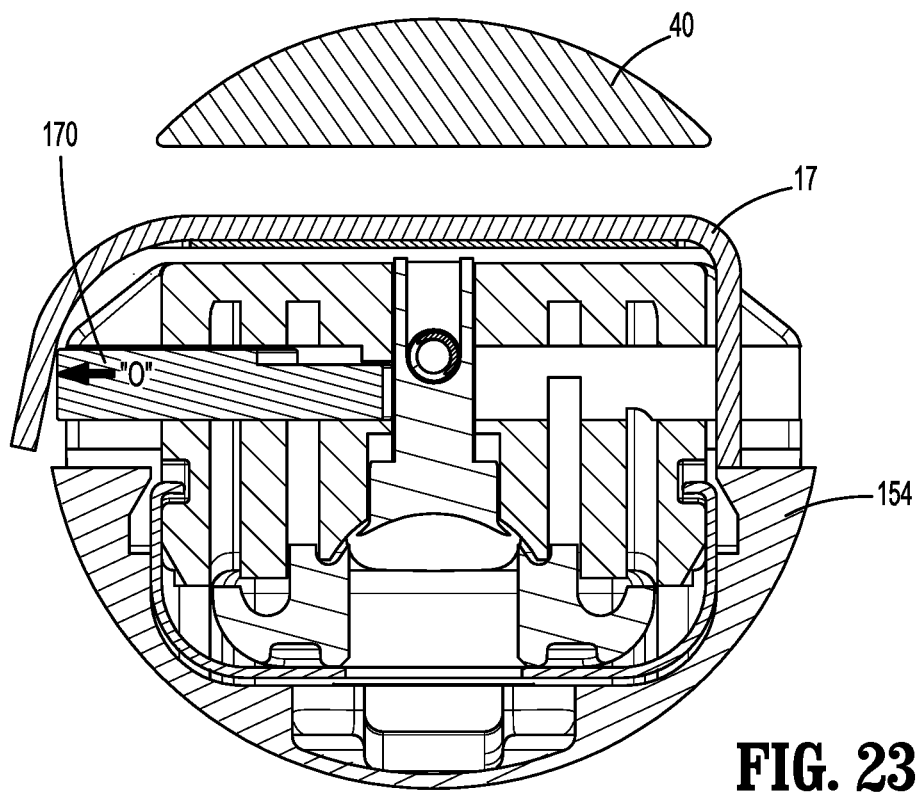
FIG. 23 is a cross-sectional view of the surgical cartridge assembly of FIG. 22 taken along section line 23-23 of FIG. 22.
Figure 24:
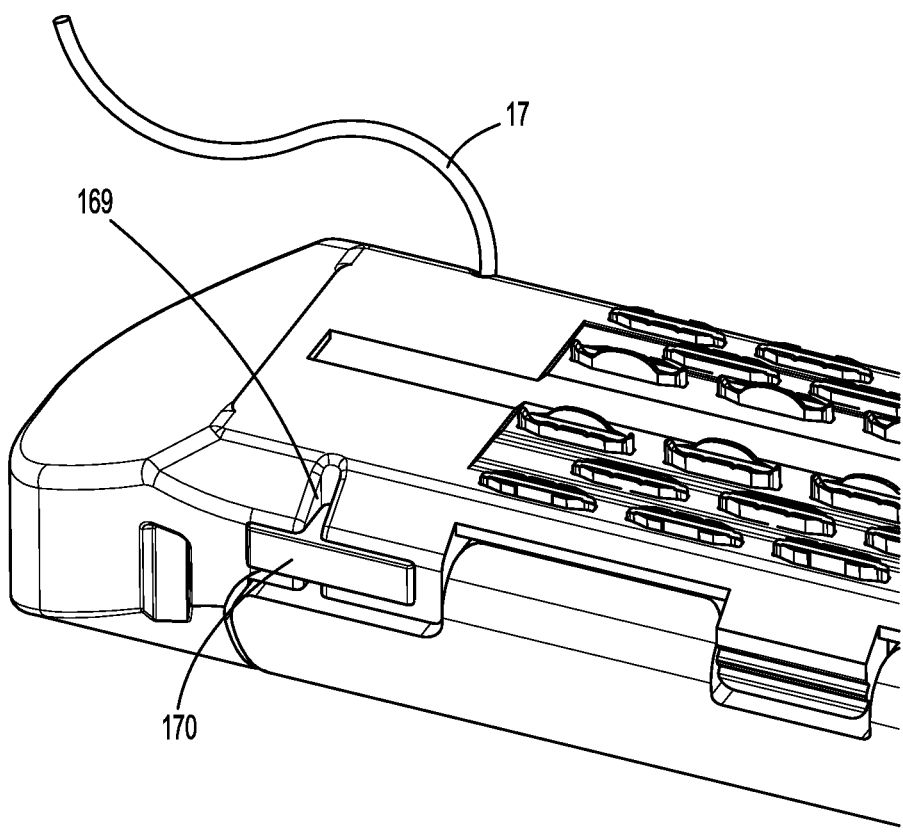
FIG. 24 is a partial perspective view of the surgical cartridge assembly of FIG. 15 illustrating severing of a suture.
Figure 25:
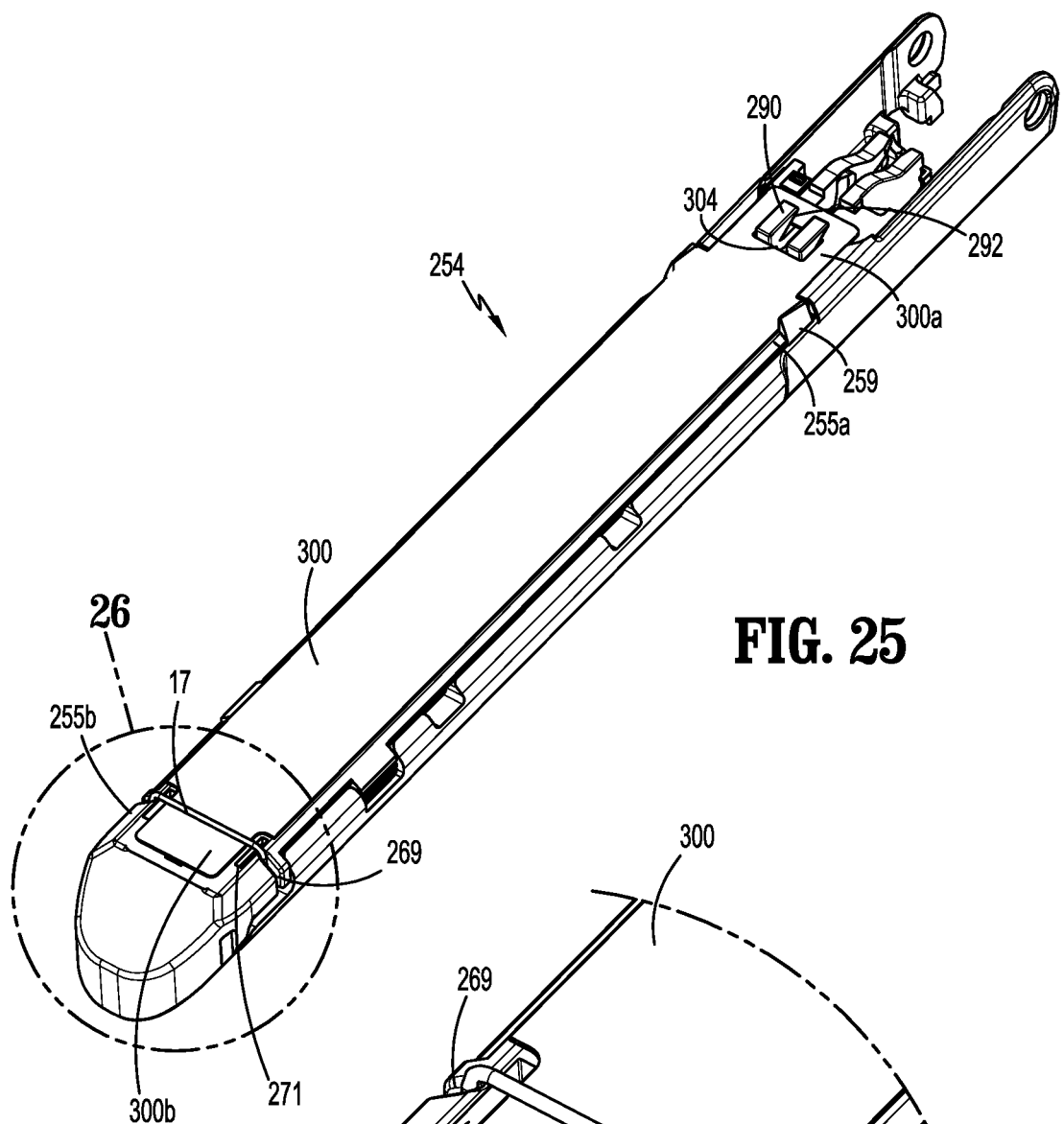
FIG. 25 is a perspective view of a staple cartridge assembly for use with the surgical stapler of FIG. 1 in accordance with yet another embodiment of the present disclosure.
Figure 26:
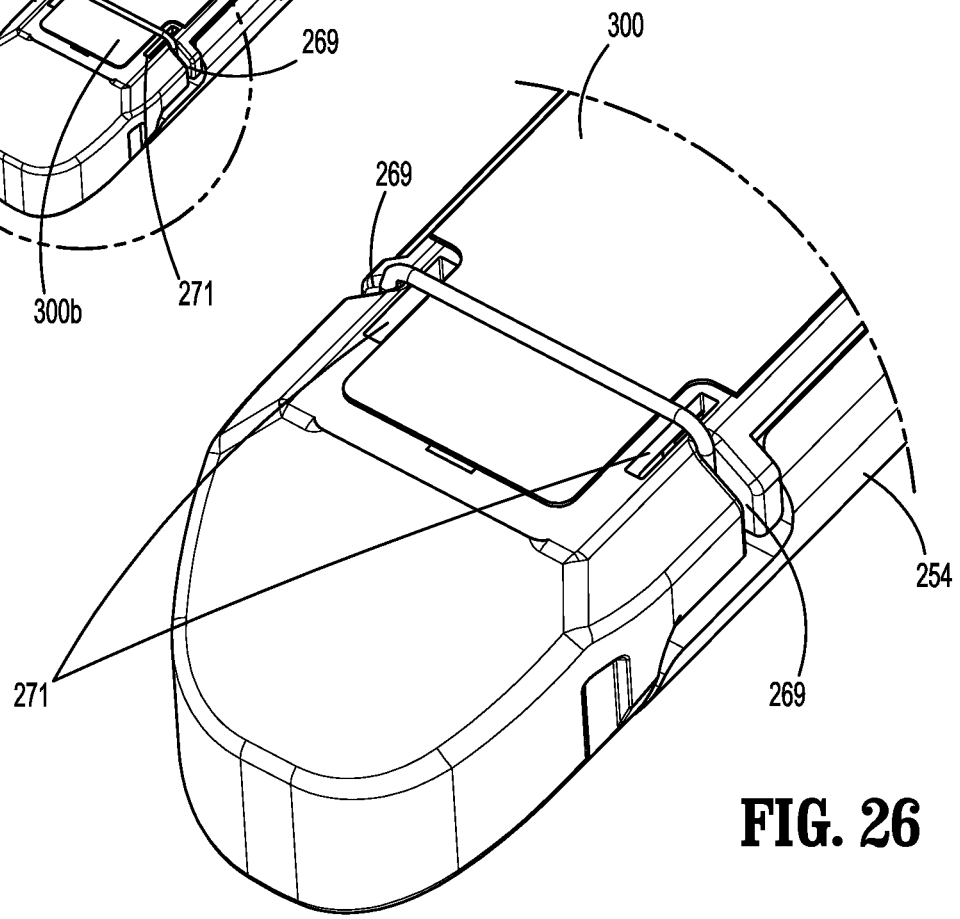
FIG. 26 is an enlarged view of the indicated area of detail of FIG. 25.

With reference now to FIGS. 20-22, the slider cam 170 is disposed inwardly of the end portions of the suture 17 secured within the respective lateral grooves 169 (FIG. 16) of the staple cartridge 154. Initially, the inner portion 177 (FIG. 18) of the slider cam 170 is disposed substantially in registration with the central longitudinal slot 157 (FIG. 20). The finger 174 extends upward from a plane defined by the main body 171 and the inner portion 177 such that the finger 174 engages an inner stop 157b to limit displacement towards the central longitudinal slot 157. Under such a configuration, the slider cam 170 is slidable between a first position in which the inner portion 177 is substantially in registration (FIG. 20) with the central longitudinal slot 157 and a second position in which the engaging surface 172 (FIG. 18) of the main body 171 is substantially flush with a lateral surface of the staple cartridge 154 (FIG. 22).

With reference now to FIGS. 20-24, initially, the slider cam 170 is disposed inwardly of the end portions of the suture 17 securing the distal portion 204 (FIG. 17) of the surgical buttress material 200 to the staple cartridge 154, whereby the end portions of the suture 17 are securely disposed within the respective lateral grooves 169 (FIG. 16) of the staple cartridge 154. As the actuation sled 166 is advanced distally, an elongate engaging portion 179 of the actuation sled 166 engages the arcuate or tapered surface 178 of the inner portion 177 (FIG. 16) of the slider cam 170, which, in turn, causes the slider cam 170 to be moved laterally outward in the direction of an arrow "O" until the hook portion 174a of the finger 174 engages the outer stop 157a. Laterally outward displacement of the slider cam 170 urges the corresponding end portion of the suture 17 out of the corresponding lateral groove 169. In this manner, one end of the suture 17 is freed from the staple cartridge 154 thereby enabling detachment of the surgical buttress material 200 from the staple cartridge 154. The method and use of the staple cartridge 154 is substantially similar to the method and use of the staple cartridge 54 described hereinabove, and thus, will not be described herein.

With reference now to FIGS. 25-31, yet another embodiment of a staple cartridge for use with the surgical stapler (FIG. 1) is shown as a staple cartridge 254. Parts of the staple cartridge 254 substantially similar to the parts of the staple cartridges 54 (FIG. 3), 154 (FIG. 15) will not be described herein to avoid obscuring the present disclosure in unnecessary detail. The staple cartridge 254 may be detachably secured to the cartridge carrier 52 (FIG. 1) by, e.g., snap fit or interference fit. The staple cartridge 254 defines staple retention slots 255 (FIG. 31) for receiving a plurality of fasteners or staples 58 (FIG. 3) and staple pushers 60 (FIG. 3) therein. A central longitudinal slot 257 (FIG. 3) is defined along a substantial length of the staple cartridge 254 to facilitate passage of the first knife blade 61 (FIG. 6) of the actuation sled 66 therethrough. In particular, proximal and distal portions 255a, 255b of the staple cartridge 254 are configured to detachably secure the surgical buttress material 300 to the staple cartridge 254. Proximal portion 255a of the staple cartridge 254 includes a pair of lateral guides 259 extending from the tissue facing surface 256. The surgical buttress material 300 is received between the lateral guides 259. In addition, the proximal portion 255a of the staple cartridge 254 includes hook portions 290 having tapered surfaces 292 configured to engage a cavity 304 defined in a proximal portion 300a of the surgical buttress material 300.

Figure 27:
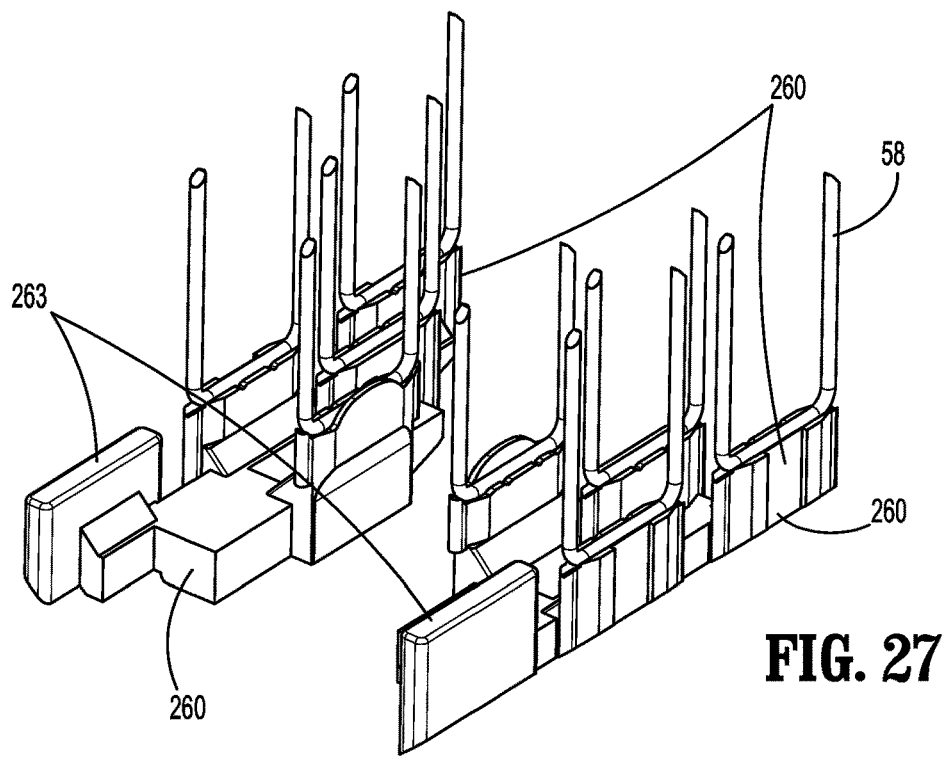
FIG. 27 is a perspective view of staple pushers and staples of the staple cartridge assembly of FIG. 25.
Figure 28:
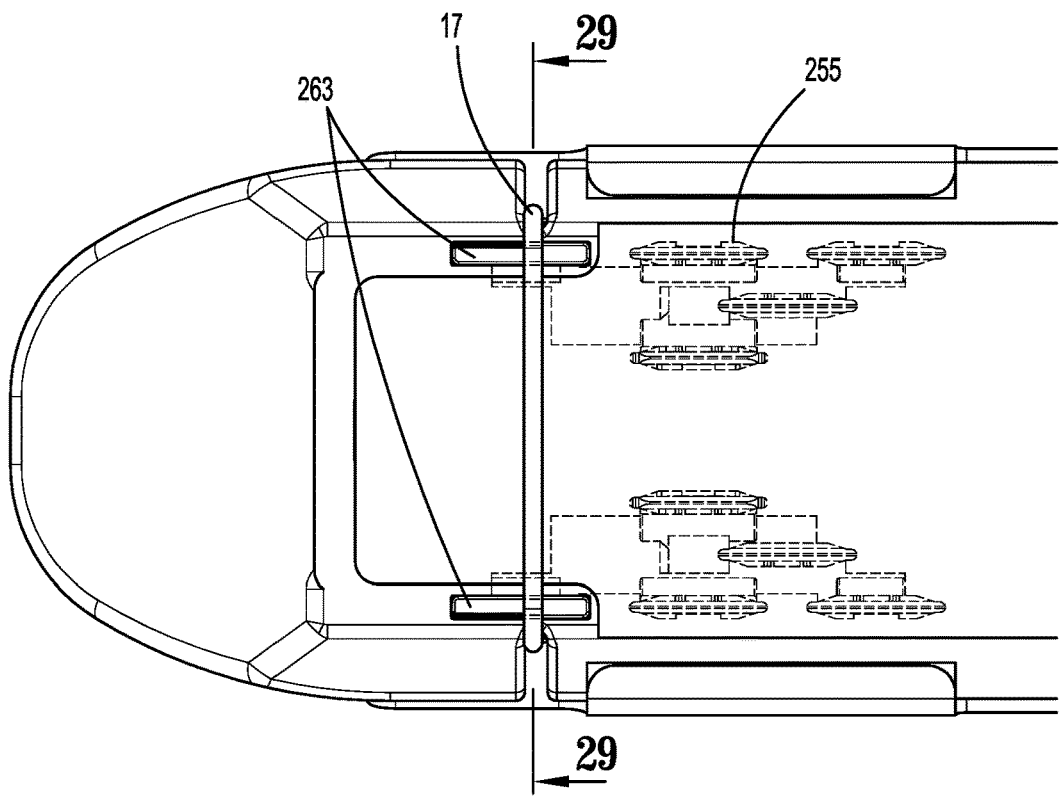
FIG. 28 is a partial top view of the staple cartridge assembly of FIG. 25 illustrating the staple pushers of FIG. 27 shown in phantom.
Figure 29:
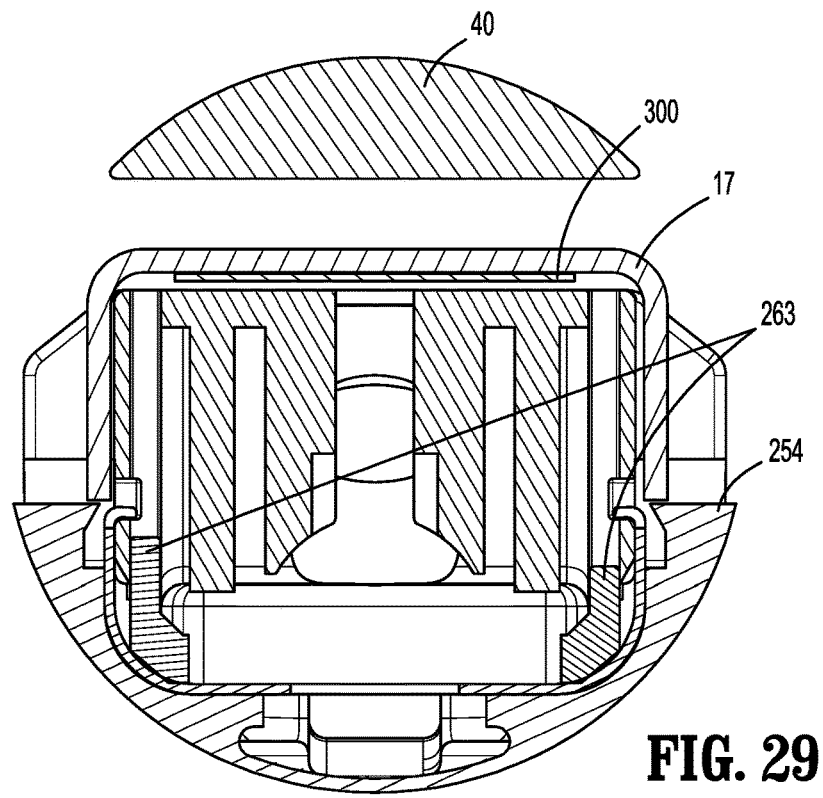
FIG. 29 is a cross-sectional view of the staple cartridge assembly of FIG. 28 taken along section line 29-29 of FIG. 28.

The distal portion 255b of the staple cartridge 254 defines opposing lateral grooves 269 configured to receive respective end portions of the suture 17 to secure the surgical buttress material 300 to the staple cartridge 254. In addition, the distal portion 255b further defines a pair of opposing slots 271 configured to receive respective lifting members 263 (FIG. 27). Under such a configuration, a portion of the surgical buttress material 300 is interposed between the opposing slots 271. The lifting members 263 may be disposed on respective distal-most pushers 260. In an embodiment, the lifting member 263 and the distal-most pushers 260 may be formed as single construct.

A portion of the surgical buttress material 300 is interposed between the slots 271 such that when the respective end portions of the suture 17 are secured to the lateral grooves 269, the suture 17 extends over the opposing slots 271. Under such a configuration, the suture 17 secures the surgical buttress material 300 to the distal portion 255b of the staple cartridge 254.

Figure 30:
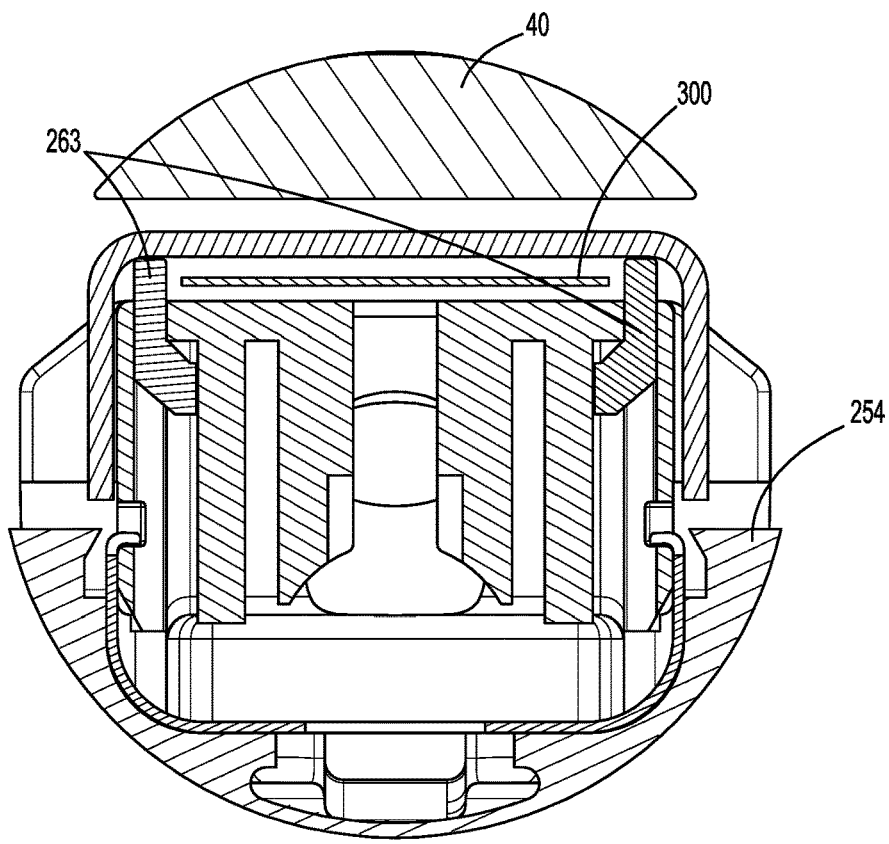
FIG. 30 is a cross-sectional view of the staple cartridge assembly of FIG. 29 illustrating actuation of lifting members.
Figure 31:
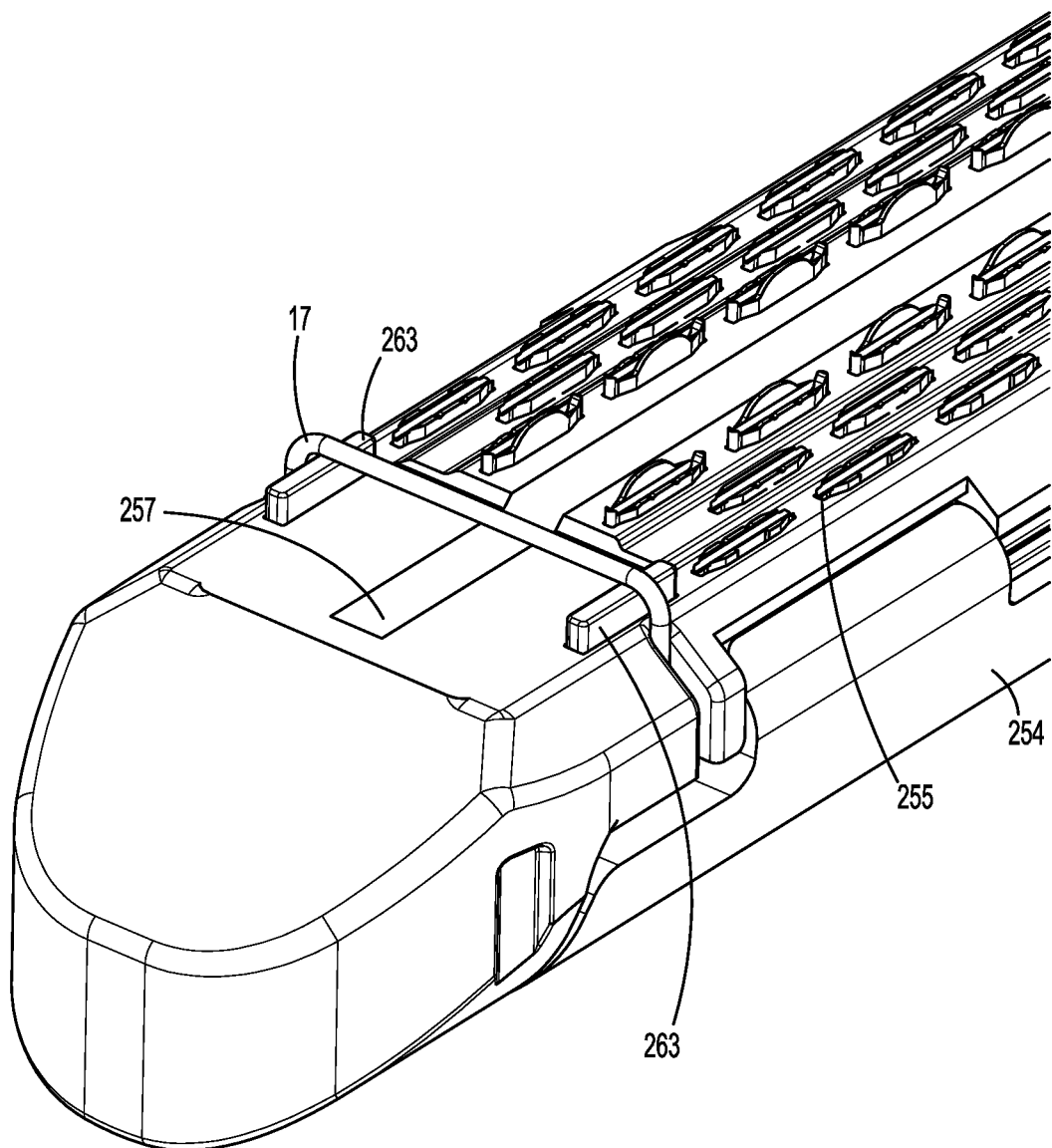
FIG. 31 is a partial perspective view of the staple cartridge assembly of FIG. 25 illustrating actuation of the lifting members.

With respect to FIGS. 30 and 31, when the lifting members 263 extend out of the respective slots 271, the lifting members 263 urge the suture 17 away from the surgical buttress material 300, e.g., towards the anvil assembly 40, such that the surgical buttress material 300 may be released from the staple cartridge 254. In an embodiment, the suture 17 may be flexible.

During operation of the surgical stapler 1, the actuation sled 66 translates through the staple cartridge 254 to advance cam wedges 68 of the actuation sled 66 into sequential contact with the staple pushers 260. This causes the staple pushers 60 to move vertically within the staple pockets 255 and urge the staples 58 from the staple pockets 255 towards the anvil assembly 40. In addition, the lifting members 263 extend out of the respective slots 271 (FIG. 26) and release the surgical buttress material 300 from the staple cartridge 254. The method and use of the staple cartridge 254 is substantially similar to the method and use of the staple cartridges 54, 154 described hereinabove, and thus, will not be described herein.

While several embodiments of the disclosure have been shown in the drawings, it is not intended that the disclosure be limited thereto, as it is intended that the disclosure be as broad in scope as the art will allow and that the specification be read likewise. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Therefore, the above description should not be construed as limiting, but merely as exemplifications of preferred embodiments. Thus, the scope of the embodiments should be determined by the appended claims and their legal equivalents, rather than by the examples given.

What is claimed is:

1. An end effector for use with a surgical stapler comprising:
   an anvil assembly;

a staple cartridge receiving channel movable relative to the anvil assembly between an approximated position and a spaced apart position; and
a staple cartridge assembly selectively receivable in the staple cartridge receiving channel, the staple cartridge assembly defining a plurality of retention slots and a longitudinally extending central knife slot, the staple cartridge assembly including:
 a plurality of staples, wherein each of the plurality of staples is disposed in a respective one of the plurality of retention slots;
 a plurality of pushers configured to eject the plurality of staples through the respective plurality of retention slots;
 an actuation sled configured for movement along a length of the staple cartridge assembly to sequentially engage the plurality of pushers to eject the plurality of staples through the respective plurality of retention slots, the actuation sled including:
  a first knife blade supported on the actuation sled; and
  a second knife blade pivotably connected to the actuation sled, the second knife blade being located proximal of the first knife blade.

2. The end effector according to claim 1, wherein the first knife blade is distally oriented.

3. The end effector according to claim 2, wherein the second knife blade is distally oriented.

4. The end effector according to claim 3, wherein the second knife blade is located proximal of a pivot axis for the second knife blade.

5. The end effector according to claim 4, wherein the first knife blade is located distally of the pivot axis of the second knife blade.

6. The end effector according to claim 5, wherein the first knife blade is located along the central knife slot of the staple cartridge assembly.

7. The end effector according to claim 6, wherein the second knife blade is located along the central knife slot of the staple cartridge assembly.

8. The end effector according to claim 7, wherein the staple cartridge assembly further comprises:
a surgical buttress material configured to be supported on a tissue facing surface of the staple cartridge assembly; and
a suture including opposing ends securely attached to opposing lateral sides of the staple cartridge assembly.

9. The end effector according to claim 8, wherein the staple cartridge assembly defines a cavity, and further comprises:
an anchoring button configured to be received in the cavity of the staple cartridge assembly such that a portion of the suture is supported in the cavity so as to be severed by the first knife blade of the actuation sled when the actuation sled is advanced distally.

10. The end effector according to claim 9, wherein the staple cartridge assembly further defines opposing lateral grooves configured to securely receive the respective opposing ends of the suture.

11. The end effector according to claim 8, wherein the second knife blade is configured to travel along the central longitudinal slot to cut the surgical buttress material and tissue in superposed relation with the tissue facing surface of the staple cartridge assembly.

12. A staple cartridge assembly configured for selective loading into a staple cartridge receiving channel of a jaw of an end effector of a surgical stapler, the staple cartridge assembly comprising:
a staple cartridge body defining a plurality of retention slots and a longitudinally extending central knife slot;
a plurality of staples, wherein each of the plurality of staples is disposed in a respective one of the plurality of retention slots;
a plurality of pushers configured to eject the plurality of staples through the respective plurality of retention slots;
an actuation sled configured for movement along a length of the staple cartridge assembly to sequentially engage the plurality of pushers to eject the plurality of staples through the respective plurality of retention slots, the actuation sled including:
 a first knife blade supported on the actuation sled; and
 a second knife blade pivotably connected to the actuation sled, the second knife blade being located proximal of the first knife blade.

13. The staple cartridge assembly according to claim 12, wherein the first knife blade is distally oriented.

14. The staple cartridge assembly according to claim 13, wherein the second knife blade is distally oriented.

15. The staple cartridge assembly according to claim 14, wherein the second knife blade is located proximal of a pivot axis for the second knife blade.

16. The staple cartridge assembly according to claim 15, wherein the first knife blade is located distally of the pivot axis of the second knife blade.

17. The staple cartridge assembly according to claim 16, wherein the first knife blade is located along the central knife slot of the staple cartridge assembly.

18. The staple cartridge assembly according to claim 17, wherein the second knife blade is located along the central knife slot of the staple cartridge assembly.

19. The end effector according to claim 18, wherein the staple cartridge assembly further comprises:
a surgical buttress material configured to be supported on a tissue facing surface of the staple cartridge assembly; and
a suture including opposing ends securely attached to opposing lateral sides of the staple cartridge assembly.

20. A staple cartridge assembly configured for selective loading into a staple cartridge receiving channel of a jaw of an end effector of a surgical stapler, the staple cartridge assembly comprising:
a staple cartridge body defining a plurality of retention slots and a longitudinally extending central knife slot;
a plurality of staples, wherein each of the plurality of staples is disposed in a respective one of the plurality of retention slots;
a plurality of pushers configured to eject the plurality of staples through the respective plurality of retention slots;
an actuation sled configured for movement along a length of the staple cartridge assembly to sequentially engage the plurality of pushers to eject the plurality of staples through the respective plurality of retention slots, the actuation sled including:
 a first knife blade positioned within the staple cartridge body; and
 a second knife blade positioned proximal of the first knife blade, wherein the second knife blade is pivotably connected to the sled, wherein the second knife blade has a retracted position wherein the second knife blade is fully contained within the staple cartridge body, and wherein the second knife blade has a deployed position wherein the at least a portion of the second knife blade projects from the staple cartridge body.

* * * * *